(12) United States Patent
Felix et al.

(10) Patent No.: US 11,116,451 B2
(45) Date of Patent: Sep. 14, 2021

(54) SUBCUTANEOUS P-WAVE CENTRIC INSERTABLE CARDIAC MONITOR WITH ENERGY HARVESTING CAPABILITIES

(71) Applicant: Bardy Diagnostics, Inc., Seattle, WA (US)

(72) Inventors: Jason Felix, Vashon Island, WA (US); Joshua Djon Green, Seattle, WA (US); Gust H. Bardy, Carnation, WA (US)

(73) Assignee: BARDY DIAGNOSTICS, INC., Bellevue, WA (US)

( * ) Notice: Subject to any disclaimer, the term of this patent is extended or adjusted under 35 U.S.C. 154(b) by 0 days.

(21) Appl. No.: 16/919,626

(22) Filed: Jul. 2, 2020

(65) Prior Publication Data
US 2021/0000418 A1    Jan. 7, 2021

Related U.S. Application Data

(60) Provisional application No. 62/870,506, filed on Jul. 3, 2019.

(51) Int. Cl.
| | | |
|---|---|---|
| A61B 5/00 | (2006.01) | |
| A61B 5/316 | (2021.01) | |
| A61B 5/349 | (2021.01) | |

(52) U.S. Cl.
CPC ............ *A61B 5/686* (2013.01); *A61B 5/0006* (2013.01); *A61B 5/0031* (2013.01); *A61B 5/316* (2021.01);
(Continued)

(58) Field of Classification Search
CPC ......... A61B 5/686; A61B 5/349; A61B 5/316; A61B 5/0006; A61B 5/0031; A61B 5/7455; A61B 5/746; A61B 2560/0219
See application file for complete search history.

(56) References Cited

U.S. PATENT DOCUMENTS

| 3,215,136 A | 11/1965 | Holter et al. |
| 3,569,852 A | 3/1971 | Berkovits |

(Continued)

FOREIGN PATENT DOCUMENTS

| DE | 19955211 | 5/2001 |
| EP | 1859833 | 11/2007 |

(Continued)

OTHER PUBLICATIONS http://web.archive.org/web/20181006234344/https:/en.wikipedia.org/wiki/Automatic_watch, cached on Oct. 6, 2018.

(Continued)

*Primary Examiner* — Carl H Layno
*Assistant Examiner* — Roland Dinga
(74) *Attorney, Agent, or Firm* — Patrick J. S. Inouye; Leonid Kisselev

(57) ABSTRACT

A P-wave centric subcutaneous insertable cardiac monitor (ICM) for use in performing long term electrocardiographic (ECG) monitoring is disclosed. The length of the monitoring performed by the ICM is extended, potentially for a life time of the patient, and the functionality of the ICM is enhanced, by including an internal energy harvesting module in the ICM. The energy harvesting module harvests energy from outside the ICM, and provides the harvested energy for powering the circuitry of the ICM, either directly or by recharging a power cell within the ICM. As the circuitry of the ICM requires a low amount of electrical power, the harvested energy can be sufficient to support the functioning of the ICM even when the electrical power stored on the ICM at the time of implantation runs out.

22 Claims, 11 Drawing Sheets

(52) U.S. Cl.
CPC .............. *A61B 5/349* (2021.01); *A61B 5/746* (2013.01); *A61B 5/7455* (2013.01); *A61B 2560/0219* (2013.01)

(56) References Cited

U.S. PATENT DOCUMENTS

| | | |
|---|---|---|
| 3,602,215 A | 8/1971 | Parnell |
| 3,699,948 A | 10/1972 | Ota et al. |
| 3,718,772 A | 2/1973 | Sanctuary |
| 3,893,453 A | 7/1975 | Goldberg |
| 4,123,785 A | 10/1978 | Cherry et al. |
| 4,151,513 A | 4/1979 | Menken et al. |
| 4,328,814 A | 5/1982 | Arkans |
| 4,441,500 A | 4/1984 | Sessions et al. |
| 4,532,934 A | 8/1985 | Kelen |
| 4,546,342 A | 10/1985 | Weaver et al. |
| 4,550,502 A | 11/1985 | Grayzel |
| 4,580,572 A | 4/1986 | Granek et al. |
| 4,635,646 A | 1/1987 | Gilles et al. |
| 4,653,022 A | 3/1987 | Koro |
| 4,716,903 A | 1/1988 | Hansen |
| 4,809,705 A | 3/1989 | Ascher |
| 4,915,656 A | 4/1990 | Alferness |
| 5,007,429 A | 4/1991 | Treatch et al. |
| 5,025,794 A | 6/1991 | Albert et al. |
| 5,107,480 A | 4/1992 | Naus |
| 5,168,876 A | 12/1992 | Quedens et al. |
| 5,215,098 A | 6/1993 | Steinhaus |
| 5,231,990 A | 8/1993 | Gauglitz |
| D341,423 S | 11/1993 | Bible |
| 5,263,481 A | 11/1993 | Axelgaard |
| 5,265,579 A | 11/1993 | Ferrari |
| 5,333,615 A | 8/1994 | Craelius et al. |
| 5,341,806 A | 8/1994 | Gadsby et al. |
| 5,348,008 A | 9/1994 | Bornn et al. |
| 5,355,891 A | 10/1994 | Wateridge et al. |
| 5,365,934 A | 11/1994 | Leon et al. |
| 5,365,935 A | 11/1994 | Righter et al. |
| 5,392,784 A | 2/1995 | Gudaitis |
| D357,069 S | 4/1995 | Plahn et al. |
| 5,402,780 A | 4/1995 | Faasse, Jr. |
| 5,402,884 A | 4/1995 | Gilman et al. |
| 5,450,845 A | 9/1995 | Axelgaard |
| 5,451,876 A | 9/1995 | Sendford et al. |
| 5,458,141 A | 10/1995 | Neil |
| 5,473,537 A | 12/1995 | Glazer et al. |
| 5,483,969 A | 1/1996 | Testerman et al. |
| 5,511,553 A | 4/1996 | Segalowitz |
| 5,540,733 A | 7/1996 | Testerman et al. |
| 5,546,952 A | 8/1996 | Erickson |
| 5,549,655 A | 8/1996 | Erickson |
| 5,579,919 A | 12/1996 | Gilman et al. |
| 5,582,181 A | 12/1996 | Ruess |
| D377,983 S | 2/1997 | Sabri et al. |
| 5,601,089 A | 2/1997 | Bledsoe et al. |
| 5,623,935 A | 4/1997 | Faisandier |
| 5,682,901 A | 11/1997 | Kamen |
| 5,697,955 A | 12/1997 | Stolte |
| 5,724,967 A | 3/1998 | Venkatachalam |
| 5,749,902 A | 5/1998 | Olsen et al. |
| 5,788,633 A | 8/1998 | Mahoney |
| 5,817,151 A | 10/1998 | Olsen et al. |
| 5,819,741 A | 10/1998 | Karlsson et al. |
| 5,850,920 A | 12/1998 | Gilman et al. |
| 5,860,918 A | 1/1999 | Schradi |
| D407,159 S | 3/1999 | Roberg |
| 5,876,351 A | 3/1999 | Rohde |
| 5,906,583 A | 5/1999 | Rogel |
| 5,951,598 A | 9/1999 | Bishay et al. |
| 5,957,857 A | 9/1999 | Hartley |
| 5,984,102 A | 11/1999 | Tay |
| 6,032,064 A | 2/2000 | Devlin et al. |
| 6,038,469 A | 3/2000 | Karlsson et al. |
| 6,101,413 A | 8/2000 | Olsen et al. |
| 6,115,638 A | 9/2000 | Groenke |
| 6,117,077 A | 9/2000 | Del Mar et al. |
| 6,134,479 A | 10/2000 | Brewer et al. |
| 6,148,233 A | 11/2000 | Owen et al. |
| 6,149,602 A | 11/2000 | Arcelus |
| 6,149,781 A | 11/2000 | Forand |
| 6,188,407 B1 | 2/2001 | Smith et al. |
| 6,190,350 B1 | 2/2001 | Davis et al. |
| D443,063 S | 5/2001 | Pisani et al. |
| 6,245,025 B1 | 6/2001 | Torok et al. |
| 6,246,330 B1 | 6/2001 | Nielsen |
| 6,249,696 B1 | 6/2001 | Olson et al. |
| D445,507 S | 7/2001 | Pisani et al. |
| 6,269,267 B1 | 7/2001 | Bardy et al. |
| 6,272,385 B1 | 8/2001 | Bishay et al. |
| 6,298,255 B1 | 10/2001 | Cordero et al. |
| 6,301,502 B1 | 10/2001 | Owen et al. |
| 6,304,773 B1 | 10/2001 | Taylor et al. |
| 6,304,780 B1 | 10/2001 | Owen et al. |
| 6,304,783 B1 | 10/2001 | Lyster et al. |
| 6,374,138 B1 | 4/2002 | Owen et al. |
| 6,381,482 B1 | 4/2002 | Jayaraman et al. |
| 6,416,471 B1 | 7/2002 | Kumar et al. |
| 6,418,342 B1 | 7/2002 | Owen et al. |
| 6,424,860 B1 | 7/2002 | Karlsson et al. |
| 6,427,083 B1 | 7/2002 | Owen et al. |
| 6,427,085 B1 | 7/2002 | Boon et al. |
| 6,454,708 B1 | 9/2002 | Ferguson et al. |
| 6,456,872 B1 | 9/2002 | Faisandier |
| 6,463,320 B1 | 10/2002 | Xue et al. |
| 6,546,285 B1 | 4/2003 | Owen et al. |
| 6,605,046 B1 | 8/2003 | Del Mar |
| 6,607,485 B2 | 8/2003 | Bardy |
| 6,611,705 B2 | 8/2003 | Hopman et al. |
| 6,671,545 B2 | 12/2003 | Fincke |
| 6,671,547 B2 | 12/2003 | Lyster et al. |
| 6,694,186 B2 | 2/2004 | Bardy |
| 6,704,595 B2 | 3/2004 | Bardy |
| 6,705,991 B2 | 3/2004 | Bardy |
| 6,719,701 B2 | 4/2004 | Lade |
| 6,754,523 B2 | 6/2004 | Toole |
| 6,782,293 B2 | 8/2004 | Dupelle et al. |
| 6,856,832 B1 | 2/2005 | Matsumura |
| 6,860,897 B2 | 3/2005 | Bardy |
| 6,866,629 B2 | 3/2005 | Bardy |
| 6,887,201 B2 | 5/2005 | Bardy |
| 6,893,397 B2 | 5/2005 | Bardy |
| 6,895,261 B1 | 5/2005 | Palamides |
| 6,904,312 B2 | 6/2005 | Bardy |
| 6,908,431 B2 | 6/2005 | Bardy |
| 6,913,577 B2 | 7/2005 | Bardy |
| 6,944,498 B2 | 9/2005 | Owen et al. |
| 6,960,167 B2 | 11/2005 | Bardy |
| 6,970,731 B1 | 11/2005 | Jayaraman et al. |
| 6,978,169 B1 | 12/2005 | Guerra |
| 6,993,377 B2 | 1/2006 | Flick et al. |
| 7,020,508 B2 | 3/2006 | Stivoric et al. |
| 7,027,864 B2 | 4/2006 | Snyder et al. |
| 7,065,401 B2 | 6/2006 | Worden |
| 7,085,601 B1 | 8/2006 | Bardy et al. |
| 7,104,955 B2 | 9/2006 | Bardy |
| 7,134,996 B2 | 11/2006 | Bardy |
| 7,137,389 B2 | 11/2006 | Berthon-Jones |
| 7,147,600 B2 | 12/2006 | Bardy |
| 7,215,991 B2 | 5/2007 | Besson et al. |
| 7,248,916 B2 | 7/2007 | Bardy |
| 7,257,438 B2 | 8/2007 | Kinast |
| 7,277,752 B2 | 10/2007 | Matos |
| 7,294,108 B1 | 11/2007 | Bornzin et al. |
| D558,882 S | 1/2008 | Brady |
| 7,328,061 B2 | 2/2008 | Rowlandson et al. |
| 7,412,395 B2 | 8/2008 | Rowlandson et al. |
| 7,429,938 B1 | 9/2008 | Corndorf |
| 7,552,031 B2 | 6/2009 | Vock et al. |
| D606,656 S | 12/2009 | Kobayashi et al. |
| 7,706,870 B2 | 4/2010 | Shieh et al. |
| 7,756,721 B1 | 7/2010 | Falchuk et al. |
| 7,787,943 B2 | 8/2010 | McDonough |
| 7,874,993 B2 | 1/2011 | Bardy |
| 7,881,785 B2 | 2/2011 | Nassif et al. |

(56) References Cited

U.S. PATENT DOCUMENTS

| | | |
|---|---|---|
| D639,437 S | 6/2011 | Bishay et al. |
| 7,959,574 B2 | 6/2011 | Bardy |
| 8,108,035 B1 | 1/2012 | Bharmi |
| 8,116,841 B2 | 2/2012 | Bly et al. |
| 8,135,459 B2 | 3/2012 | Bardy et al. |
| 8,172,761 B1 | 5/2012 | Rulkov et al. |
| 8,180,425 B2 | 5/2012 | Selvitelli et al. |
| 8,200,320 B2 | 6/2012 | Kovacs |
| 8,231,539 B2 | 7/2012 | Bardy |
| 8,231,540 B2 | 7/2012 | Bardy |
| 8,239,012 B2 | 8/2012 | Felix et al. |
| 8,249,686 B2 | 8/2012 | Libbus et al. |
| 8,260,414 B2 | 9/2012 | Nassif et al. |
| 8,266,008 B1 | 9/2012 | Siegal et al. |
| 8,277,378 B2 | 10/2012 | Bardy |
| 8,285,356 B2 | 10/2012 | Bly et al. |
| 8,285,370 B2 | 10/2012 | Felix et al. |
| 8,308,650 B2 | 11/2012 | Bardy |
| 8,366,629 B2 | 2/2013 | Bardy |
| 8,374,688 B2 | 2/2013 | Libbus et al. |
| 8,412,317 B2 | 4/2013 | Mazar |
| 8,460,189 B2 | 6/2013 | Libbus et al. |
| 8,473,047 B2 | 6/2013 | Chakravarthy et al. |
| 8,478,418 B2 | 7/2013 | Fahey |
| 8,538,503 B2 | 9/2013 | Kumar et al. |
| 8,554,311 B2 | 10/2013 | Warner et al. |
| 8,560,046 B2 | 10/2013 | Kumar et al. |
| 8,591,430 B2 | 11/2013 | Amurthur et al. |
| 8,594,763 B1 | 11/2013 | Bibian et al. |
| 8,600,486 B2 | 12/2013 | Kaib et al. |
| 8,613,708 B2 | 12/2013 | Bishay et al. |
| 8,613,709 B2 | 12/2013 | Bishay et al. |
| 8,620,418 B1 | 12/2013 | Kuppuraj et al. |
| 8,626,277 B2 | 1/2014 | Felix et al. |
| 8,628,020 B2 | 1/2014 | Beck |
| 8,668,653 B2 | 3/2014 | Nagata et al. |
| 8,684,925 B2 | 4/2014 | Manicka et al. |
| 8,688,190 B2 | 4/2014 | Libbus et al. |
| 8,718,752 B2 | 5/2014 | Libbus et al. |
| 8,744,561 B2 | 6/2014 | Fahey |
| 8,774,932 B2 | 7/2014 | Fahey |
| 8,790,257 B2 | 7/2014 | Libbus et al. |
| 8,790,259 B2 | 7/2014 | Katra et al. |
| 8,795,174 B2 | 8/2014 | Manicka et al. |
| 8,798,729 B2 | 8/2014 | Kaib et al. |
| 8,798,734 B2 | 8/2014 | Kuppuraj et al. |
| 8,818,478 B2 | 8/2014 | Scheffler et al. |
| 8,818,481 B2 | 8/2014 | Bly et al. |
| 8,823,490 B2 | 9/2014 | Libbus et al. |
| 8,938,287 B2 | 1/2015 | Felix et al. |
| 8,948,935 B1 | 2/2015 | Peeters |
| 8,965,492 B2 | 2/2015 | Baker et al. |
| 9,066,664 B2 | 6/2015 | Karjalainen |
| 9,155,484 B2 | 10/2015 | Baker et al. |
| 9,204,813 B2 | 12/2015 | Kaib et al. |
| 9,241,649 B2 | 1/2016 | Kumar et al. |
| 9,259,154 B2 | 2/2016 | Miller et al. |
| 9,277,864 B2 | 3/2016 | Yang et al. |
| 9,339,202 B2 | 5/2016 | Brockway et al. |
| 9,375,179 B2 | 6/2016 | Schultz et al. |
| 9,414,786 B1 | 8/2016 | Brockway et al. |
| 9,439,566 B2 | 9/2016 | Arne et al. |
| 9,597,004 B2 | 3/2017 | Hughes et al. |
| 9,603,542 B2 | 3/2017 | Veen et al. |
| 9,700,222 B2 | 7/2017 | Quinlan et al. |
| 9,770,182 B2 | 9/2017 | Bly et al. |
| 10,034,614 B2 | 7/2018 | Edic et al. |
| 10,045,708 B2 | 8/2018 | Dusan |
| 10,049,182 B2 | 8/2018 | Chefles et al. |
| 10,548,632 B2 | 2/2020 | Sick et al. |
| 2002/0013538 A1 | 1/2002 | Teller |
| 2002/0013717 A1 | 1/2002 | Ando et al. |
| 2002/0016798 A1 | 2/2002 | Sakai |
| 2002/0082867 A1 | 6/2002 | MacCarter et al. |
| 2002/0103422 A1 | 8/2002 | Harder et al. |
| 2002/0109621 A1 | 8/2002 | Khair et al. |
| 2002/0120310 A1 | 8/2002 | Linden et al. |
| 2002/0128686 A1 | 9/2002 | Minogue et al. |
| 2002/0184055 A1 | 12/2002 | Naghavi et al. |
| 2002/0193668 A1 | 12/2002 | Munneke |
| 2003/0004547 A1 | 1/2003 | Owen et al. |
| 2003/0028811 A1 | 2/2003 | Walker et al. |
| 2003/0073916 A1 | 4/2003 | Yonce |
| 2003/0083559 A1 | 5/2003 | Thompson |
| 2003/0097078 A1 | 5/2003 | Maeda |
| 2003/0139785 A1 | 7/2003 | Riff et al. |
| 2003/0149349 A1 | 8/2003 | Jensen |
| 2003/0176802 A1 | 9/2003 | Galen et al. |
| 2003/0211797 A1 | 11/2003 | Hill et al. |
| 2004/0008123 A1 | 1/2004 | Carrender |
| 2004/0019288 A1 | 1/2004 | Kinast |
| 2004/0034284 A1 | 2/2004 | Aversano et al. |
| 2004/0049120 A1 | 3/2004 | Cao et al. |
| 2004/0049132 A1 | 3/2004 | Barron et al. |
| 2004/0073127 A1 | 4/2004 | Istvan et al. |
| 2004/0087836 A1 | 5/2004 | Green et al. |
| 2004/0088019 A1 | 5/2004 | Rueter et al. |
| 2004/0093192 A1 | 5/2004 | Hasson et al. |
| 2004/0116784 A1 | 6/2004 | Gavish |
| 2004/0148194 A1 | 7/2004 | Wellons et al. |
| 2004/0163034 A1 | 8/2004 | Colbath et al. |
| 2004/0167416 A1 | 8/2004 | Lee |
| 2004/0199140 A1 | 10/2004 | Rue et al. |
| 2004/0207530 A1 | 10/2004 | Nielsen |
| 2004/0210165 A1 | 10/2004 | Marmaropoulos et al. |
| 2004/0236202 A1 | 11/2004 | Burton |
| 2004/0243435 A1 | 12/2004 | Williams |
| 2004/0256453 A1 | 12/2004 | Lammle |
| 2004/0260188 A1 | 12/2004 | Syed et al. |
| 2004/0260192 A1 | 12/2004 | Yamamoto |
| 2005/0010139 A1 | 1/2005 | Aminian et al. |
| 2005/0096717 A1 | 5/2005 | Bishay et al. |
| 2005/0101875 A1 | 5/2005 | Semler et al. |
| 2005/0108055 A1 | 5/2005 | Ott et al. |
| 2005/0113661 A1 | 5/2005 | Nazeri |
| 2005/0151640 A1 | 7/2005 | Hastings |
| 2005/0154267 A1 | 7/2005 | Bardy |
| 2005/0182308 A1 | 8/2005 | Bardy |
| 2005/0182309 A1 | 8/2005 | Bardy |
| 2005/0215918 A1 | 9/2005 | Frantz et al. |
| 2005/0222513 A1 | 10/2005 | Hadley et al. |
| 2005/0228243 A1 | 10/2005 | Bardy |
| 2005/0245839 A1 | 11/2005 | Stivoric et al. |
| 2005/0261564 A1 | 11/2005 | Ryu et al. |
| 2005/0275416 A1 | 12/2005 | Hervieux et al. |
| 2006/0025696 A1 | 2/2006 | Kurzweil et al. |
| 2006/0025824 A1 | 2/2006 | Freeman et al. |
| 2006/0030767 A1 | 2/2006 | Lang et al. |
| 2006/0030904 A1 | 2/2006 | Quiles |
| 2006/0041201 A1 | 2/2006 | Behbehani et al. |
| 2006/0084883 A1 | 4/2006 | Linker |
| 2006/0100530 A1 | 5/2006 | Kliot et al. |
| 2006/0111642 A1 | 5/2006 | Baura et al. |
| 2006/0111943 A1 | 5/2006 | Wu |
| 2006/0122469 A1 | 6/2006 | Martel |
| 2006/0124193 A1 | 6/2006 | Orr et al. |
| 2006/0224072 A1 | 10/2006 | Shennib |
| 2006/0229522 A1 | 10/2006 | Barr |
| 2006/0235320 A1 | 10/2006 | Tan et al. |
| 2006/0253006 A1 | 11/2006 | Bardy |
| 2006/0264730 A1 | 11/2006 | Stivoric et al. |
| 2006/0264767 A1 | 11/2006 | Shennib |
| 2007/0003115 A1 | 1/2007 | Patton et al. |
| 2007/0038057 A1 | 2/2007 | Nam et al. |
| 2007/0050209 A1 | 3/2007 | Yered |
| 2007/0078324 A1 | 4/2007 | Wijisiriwardana |
| 2007/0078354 A1 | 4/2007 | Holland |
| 2007/0088406 A1 | 4/2007 | Bennett et al. |
| 2007/0089800 A1 | 4/2007 | Sharma |
| 2007/0093719 A1 | 4/2007 | Nichols, Jr. et al. |
| 2007/0100248 A1 | 5/2007 | Van Dam et al. |
| 2007/0100667 A1 | 5/2007 | Bardy |
| 2007/0123801 A1 | 5/2007 | Goldberger et al. |
| 2007/0131595 A1 | 6/2007 | Jansson et al. |

(56) References Cited

U.S. PATENT DOCUMENTS

| | | |
|---|---|---|
| 2007/0136091 A1 | 6/2007 | McTaggart |
| 2007/0179357 A1 | 8/2007 | Bardy |
| 2007/0185390 A1 | 8/2007 | Perkins et al. |
| 2007/0203415 A1 | 8/2007 | Bardy |
| 2007/0203423 A1 | 8/2007 | Bardy |
| 2007/0208232 A1 | 9/2007 | Kovacs |
| 2007/0208233 A1 | 9/2007 | Kovacs |
| 2007/0208266 A1 | 9/2007 | Hadley |
| 2007/0225611 A1 | 9/2007 | Kumar et al. |
| 2007/0244405 A1 | 10/2007 | Xue et al. |
| 2007/0249946 A1 | 10/2007 | Kumar et al. |
| 2007/0255153 A1 | 11/2007 | Kumar et al. |
| 2007/0265510 A1 | 11/2007 | Bardy |
| 2007/0270678 A1 | 11/2007 | Fadem |
| 2007/0276270 A1 | 11/2007 | Tran |
| 2007/0276275 A1 | 11/2007 | Proctor et al. |
| 2007/0293738 A1 | 12/2007 | Bardy |
| 2007/0293739 A1 | 12/2007 | Bardy |
| 2007/0293740 A1 | 12/2007 | Bardy |
| 2007/0293741 A1 | 12/2007 | Bardy |
| 2007/0293772 A1 | 12/2007 | Bardy |
| 2007/0299325 A1 | 12/2007 | Farrell et al. |
| 2007/0299617 A1 | 12/2007 | Willis |
| 2008/0027337 A1 | 1/2008 | Dugan |
| 2008/0027339 A1 | 1/2008 | Nagai et al. |
| 2008/0051668 A1 | 2/2008 | Bardy |
| 2008/0058661 A1 | 3/2008 | Bardy |
| 2008/0143080 A1 | 3/2008 | Burr |
| 2008/0088467 A1 | 4/2008 | Al-Ali et al. |
| 2008/0091089 A1 | 4/2008 | Guillory et al. |
| 2008/0091097 A1 | 4/2008 | Linti et al. |
| 2008/0108890 A1 | 5/2008 | Teng et al. |
| 2008/0114232 A1 | 5/2008 | Gazit |
| 2008/0139953 A1 | 6/2008 | Baker et al. |
| 2008/0177168 A1 | 7/2008 | Callahan et al. |
| 2008/0194927 A1 | 8/2008 | KenKnight et al. |
| 2008/0208009 A1 | 8/2008 | Shklarski |
| 2008/0208014 A1 | 8/2008 | KenKnight et al. |
| 2008/0284599 A1 | 11/2008 | Zdeblick et al. |
| 2008/0288026 A1 | 11/2008 | Cross et al. |
| 2008/0294024 A1 | 11/2008 | Cosentino et al. |
| 2008/0306359 A1 | 12/2008 | Zdeblick et al. |
| 2008/0309481 A1 | 12/2008 | Tanaka et al. |
| 2008/0312522 A1 | 12/2008 | Rowlandson et al. |
| 2009/0009342 A1 | 1/2009 | Karjalainen |
| 2009/0012412 A1 | 1/2009 | Wiesel |
| 2009/0012979 A1 | 1/2009 | Bateni et al. |
| 2009/0054737 A1 | 2/2009 | Magar et al. |
| 2009/0054952 A1 | 2/2009 | Glukhovsky et al. |
| 2009/0062670 A1 | 3/2009 | Sterling |
| 2009/0062897 A1 | 3/2009 | Axelgaard |
| 2009/0069867 A1 | 3/2009 | KenKnight et al. |
| 2009/0073991 A1 | 3/2009 | Landrum et al. |
| 2009/0076336 A1 | 3/2009 | Mazar et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076346 A1 | 3/2009 | James et al. |
| 2009/0076349 A1 | 3/2009 | Libbus et al. |
| 2009/0076397 A1 | 3/2009 | Libbus et al. |
| 2009/0076401 A1 | 3/2009 | Mazar et al. |
| 2009/0076559 A1 | 3/2009 | Libbus et al. |
| 2009/0076364 A1 | 4/2009 | Libbus et al. |
| 2009/0088652 A1 | 4/2009 | Tremblay |
| 2009/0093687 A1 | 4/2009 | Telfort et al. |
| 2009/0112116 A1 | 4/2009 | Lee et al. |
| 2009/0131759 A1 | 5/2009 | Sims et al. |
| 2009/0156908 A1 | 6/2009 | Belalcazar et al. |
| 2009/0216132 A1 | 8/2009 | Orbach |
| 2009/0270708 A1 | 10/2009 | Shen et al. |
| 2009/0270747 A1 | 10/2009 | Van Dam et al. |
| 2009/0292194 A1 | 11/2009 | Libbus et al. |
| 2010/0007413 A1 | 1/2010 | Herleikson et al. |
| 2010/0022863 A1 | 1/2010 | Mogensen et al. |
| 2010/0022897 A1 | 1/2010 | Parker et al. |
| 2010/0056877 A1 | 3/2010 | Fein et al. |
| 2010/0056881 A1 | 3/2010 | Libbus et al. |
| 2010/0076517 A1* | 3/2010 | Imran .................. A61N 1/3629 607/35 |
| 2010/0081913 A1 | 4/2010 | Cross et al. |
| 2010/0137694 A1* | 6/2010 | Irazoqui .............. A61B 5/0031 600/302 |
| 2010/0174229 A1 | 7/2010 | Hsu et al. |
| 2010/0177100 A1 | 7/2010 | Carnes et al. |
| 2010/0185063 A1 | 7/2010 | Bardy |
| 2010/0185076 A1 | 7/2010 | Jeong et al. |
| 2010/0191154 A1 | 7/2010 | Berger et al. |
| 2010/0191310 A1 | 7/2010 | Bly |
| 2010/0223020 A1 | 9/2010 | Goetz |
| 2010/0234697 A1 | 9/2010 | Walter et al. |
| 2010/0234715 A1 | 9/2010 | Shin et al. |
| 2010/0234716 A1 | 9/2010 | Engel |
| 2010/0280366 A1 | 11/2010 | Arne et al. |
| 2010/0298720 A1* | 11/2010 | Potkay .................. A61B 5/6862 600/485 |
| 2010/0312188 A1 | 12/2010 | Robertson et al. |
| 2010/0324384 A1 | 12/2010 | Moon et al. |
| 2011/0021937 A1 | 1/2011 | Hugh et al. |
| 2011/0054286 A1 | 3/2011 | Crosby et al. |
| 2011/0060215 A1 | 3/2011 | Tupin et al. |
| 2011/0066041 A1 | 3/2011 | Pandia et al. |
| 2011/0077497 A1 | 3/2011 | Oster et al. |
| 2011/0105861 A1 | 5/2011 | Derchak et al. |
| 2011/0144470 A1 | 6/2011 | Mazar et al. |
| 2011/0160548 A1 | 6/2011 | Forster |
| 2011/0224564 A1 | 9/2011 | Moon et al. |
| 2011/0237922 A1 | 9/2011 | Parker, III et al. |
| 2011/0237924 A1 | 9/2011 | McGusty et al. |
| 2011/0245699 A1 | 10/2011 | Snell et al. |
| 2011/0245711 A1 | 10/2011 | Katra et al. |
| 2011/0288605 A1 | 11/2011 | Kaib et al. |
| 2011/0313305 A1 | 12/2011 | Rantala |
| 2012/0003933 A1 | 1/2012 | Baker et al. |
| 2012/0029300 A1 | 2/2012 | Paquet |
| 2012/0029306 A1 | 2/2012 | Paquet et al. |
| 2012/0029315 A1 | 2/2012 | Raptis et al. |
| 2012/0029316 A1 | 2/2012 | Raptis et al. |
| 2012/0035432 A1 | 2/2012 | Katra et al. |
| 2012/0059668 A1 | 3/2012 | Baldock et al. |
| 2012/0078127 A1 | 3/2012 | McDonald et al. |
| 2012/0088998 A1 | 4/2012 | Bardy et al. |
| 2012/0088999 A1 | 4/2012 | Bishay et al. |
| 2012/0089000 A1 | 4/2012 | Bishay et al. |
| 2012/0089001 A1 | 4/2012 | Bishay et al. |
| 2012/0089037 A1 | 4/2012 | Bishay et al. |
| 2012/0089412 A1 | 4/2012 | Bishay et al. |
| 2012/0089417 A1 | 4/2012 | Bardy et al. |
| 2012/0095352 A1 | 4/2012 | Tran |
| 2012/0101358 A1 | 4/2012 | Boettcher et al. |
| 2012/0101396 A1 | 4/2012 | Solosko et al. |
| 2012/0165645 A1 | 6/2012 | Russel et al. |
| 2012/0306662 A1 | 6/2012 | Vosch et al. |
| 2012/0172695 A1 | 7/2012 | Ko et al. |
| 2012/0179665 A1 | 7/2012 | Baarman et al. |
| 2012/0184207 A1 | 7/2012 | Gaines |
| 2012/0220835 A1 | 8/2012 | Chung |
| 2012/0232929 A1 | 9/2012 | Experton |
| 2012/0238910 A1 | 9/2012 | Nordstrom |
| 2012/0253847 A1 | 10/2012 | Dell'Anno et al. |
| 2012/0302906 A1 | 11/2012 | Felix et al. |
| 2012/0330126 A1 | 12/2012 | Hoppe et al. |
| 2013/0041272 A1 | 2/2013 | Javier et al. |
| 2013/0077263 A1 | 3/2013 | Oleson et al. |
| 2013/0079611 A1 | 3/2013 | Besko |
| 2013/0079618 A1 | 3/2013 | Sandmore et al. |
| 2013/0085347 A1 | 4/2013 | Manicka et al. |
| 2013/0085403 A1 | 4/2013 | Gunderson et al. |
| 2013/0087609 A1 | 4/2013 | Nichol et al. |
| 2013/0096395 A1 | 4/2013 | Katra et al. |
| 2013/0116533 A1 | 5/2013 | Lian et al. |
| 2013/0123651 A1 | 5/2013 | Bardy |
| 2013/0124891 A1 | 5/2013 | Donaldson |
| 2013/0131530 A1 | 5/2013 | Brockway et al. |
| 2013/0158361 A1 | 6/2013 | Bardy |

(56) References Cited

U.S. PATENT DOCUMENTS

| | | |
|---|---|---|
| 2013/0172763 A1 | 7/2013 | Wheeler |
| 2013/0197380 A1 | 8/2013 | Oral et al. |
| 2013/0225963 A1 | 8/2013 | Kodandaramaiah et al. |
| 2013/0225966 A1 | 8/2013 | Macia Barber et al. |
| 2013/0231947 A1 | 9/2013 | Shusterman |
| 2013/0243105 A1 | 9/2013 | Lei et al. |
| 2013/0274565 A1 | 10/2013 | Langer et al. |
| 2013/0274584 A1 | 10/2013 | Finlay et al. |
| 2013/0275158 A1 | 10/2013 | Fahey |
| 2013/0324809 A1 | 12/2013 | Lisogurski et al. |
| 2013/0324855 A1 | 12/2013 | Lisogurski et al. |
| 2013/0324856 A1 | 12/2013 | Lisogurski et al. |
| 2013/0325081 A1 | 12/2013 | Karst et al. |
| 2013/0325359 A1 | 12/2013 | Jarverud et al. |
| 2013/0331665 A1 | 12/2013 | Libbus et al. |
| 2013/0338448 A1 | 12/2013 | Libbus et al. |
| 2013/0338472 A1 | 12/2013 | Macia Barber et al. |
| 2014/0002234 A1 | 1/2014 | Alwan |
| 2014/0005502 A1 | 1/2014 | Klap et al. |
| 2014/0012154 A1 | 1/2014 | Mazar et al. |
| 2014/0031663 A1 | 1/2014 | Gallego |
| 2014/0056452 A1 | 2/2014 | Moss et al. |
| 2014/0088399 A1 | 3/2014 | Lian et al. |
| 2014/0107509 A1 | 4/2014 | Banet et al. |
| 2014/0140359 A1 | 5/2014 | Kalevo et al. |
| 2014/0180027 A1 | 6/2014 | Buller |
| 2014/0189928 A1 | 7/2014 | Oleson et al. |
| 2014/0194760 A1 | 7/2014 | Albert |
| 2014/0206977 A1 | 7/2014 | Bahney et al. |
| 2014/0214134 A1 | 7/2014 | Peterson |
| 2014/0215246 A1 | 7/2014 | Lee et al. |
| 2014/0249852 A1 | 9/2014 | Proud |
| 2014/0296651 A1 | 10/2014 | Stone |
| 2014/0297310 A1 | 10/2014 | Collins |
| 2014/0324067 A1 | 10/2014 | Emken et al. |
| 2014/0343390 A1 | 11/2014 | Berzowska et al. |
| 2014/0358193 A1 | 12/2014 | Lyons et al. |
| 2014/0364756 A1 | 12/2014 | Brockway et al. |
| 2015/0048836 A1 | 2/2015 | Guthrie et al. |
| 2015/0051472 A1 | 2/2015 | Wang et al. |
| 2015/0065842 A1 | 3/2015 | Lee et al. |
| 2015/0094558 A1 | 4/2015 | Russell |
| 2015/0142090 A1 | 5/2015 | Duijsens et al. |
| 2015/0164349 A1 | 6/2015 | Gopalakrishnan et al. |
| 2015/0165211 A1 | 6/2015 | Naqvi et al. |
| 2015/0177175 A1 | 6/2015 | Elder et al. |
| 2015/0250422 A1 | 9/2015 | Bay |
| 2015/0257670 A1 | 9/2015 | Ortega et al. |
| 2015/0305676 A1 | 11/2015 | Shoshani |
| 2015/0335285 A1* | 11/2015 | Poon ............... A61B 5/686 600/301 |
| 2015/0359489 A1 | 12/2015 | Baudenbacher et al. |
| 2016/0066850 A1 | 3/2016 | Brockway et al. |
| 2016/0135746 A1 | 5/2016 | Kumar et al. |
| 2016/0144190 A1 | 5/2016 | Cao et al. |
| 2016/0144192 A1 | 5/2016 | Sanghera et al. |
| 2016/0150982 A1 | 6/2016 | Roy |
| 2016/0217691 A1 | 7/2016 | Kadobayashi et al. |
| 2016/0235318 A1 | 8/2016 | Sarkar |
| 2016/0235346 A1 | 8/2016 | Liu et al. |
| 2017/0056650 A1 | 3/2017 | Cohen et al. |
| 2017/0112399 A1 | 4/2017 | Brisben et al. |
| 2017/0156592 A1 | 6/2017 | Fu |
| 2017/0281032 A1 | 10/2017 | Weinberg et al. |
| 2017/0281033 A1 | 10/2017 | Higgins et al. |
| 2017/0354365 A1 | 12/2017 | Zhou |
| 2017/0366921 A1 | 12/2017 | Pflugh et al. |
| 2018/0020931 A1* | 1/2018 | Shusterman ....... A61B 5/02116 600/483 |
| 2018/0042552 A1 | 2/2018 | Li et al. |
| 2018/0078771 A1 | 3/2018 | Koop et al. |
| 2018/0116537 A1 | 5/2018 | Sullivan et al. |
| 2018/0192965 A1 | 7/2018 | Rose et al. |
| 2018/0256108 A1 | 9/2018 | Au-Yeung et al. |
| 2018/0264258 A1 | 9/2018 | Cheng et al. |
| 2018/0333058 A1 | 11/2018 | Coulon et al. |
| 2019/0021671 A1 | 1/2019 | Kumar et al. |
| 2019/0046038 A1 | 2/2019 | Weinstein et al. |
| 2019/0059763 A1 | 2/2019 | Shakur et al. |
| 2019/0069815 A1 | 3/2019 | Burnes et al. |
| 2019/0167139 A1* | 6/2019 | Bardy ................. A61B 5/0205 |
| 2019/0336032 A1 | 11/2019 | Gill et al. |
| 2020/0038671 A1 | 2/2020 | Schulhauser et al. |

FOREIGN PATENT DOCUMENTS

| | | |
|---|---|---|
| EP | 2438851 | 4/2012 |
| EP | 2438852 | 4/2012 |
| EP | 2465415 | 6/2012 |
| EP | 2589333 | 5/2013 |
| JP | H06319711 | 11/1994 |
| JP | H11188015 | 7/1999 |
| JP | 2004129788 | 4/2004 |
| JP | 2007082938 | 4/2007 |
| JP | 2009219554 | 10/2009 |
| WO | 199852463 | 11/1998 |
| WO | 00/78213 | 12/2000 |
| WO | 2003032192 | 4/2003 |
| WO | 2006009767 | 1/2006 |
| WO | 2006014806 | 2/2006 |
| WO | 2007066270 | 6/2007 |
| WO | 2007092543 | 8/2007 |
| WO | 2008010216 | 1/2008 |
| WO | 2008057884 | 5/2008 |
| WO | 2008092098 | 7/2008 |
| WO | 2009036306 | 3/2009 |
| WO | 2009036313 | 3/2009 |
| WO | 2009036327 | 3/2009 |
| WO | 2009112976 | 9/2009 |
| WO | 2009112978 | 9/2009 |
| WO | 2009112979 | 9/2009 |
| WO | 2009142975 | 11/2009 |
| WO | 2010066507 | 6/2010 |
| WO | 2010105045 | 6/2010 |
| WO | 2011047207 | 4/2011 |
| WO | 2012140559 | 10/2012 |
| WO | 2012146957 | 11/2012 |
| WO | 2017072250 | 5/2017 |
| WO | 2019030746 | 2/2019 |
| WO | 2019073288 | 4/2019 |

OTHER PUBLICATIONS

15 Of The Hottest Wearable Gadgets, URL <http://thehottestgadgets.com/2008/09/the-15-hottest-wearable-gadgets-001253> (Web page cached on Sep. 27, 2008).

Alivecor, URL <http://www.businesswire.com/news/home/20121203005545/en/AliveCor%E2%80%99s-Heart-Monitor-Phone-Receives-FDA-Clearance#.U7rtq7FVTyF> (Dec. 3, 2012).

Bharadwaj et al., Techniques for Accurate ECG signal processing, EE Times, URL <www.eetimes.com/document.asp?doc_id=1278571> (Feb. 14, 2011).

Chen et al. "Monitoring Body Temperature of Newborn Infants at Neonatal Intensive Care Units Using Wearable Sensors," BodyNets 2010, Corfu Island, Greece. Sep. 10-12, 1210.

Epstein, Andrew E. et al.; ACC/AHA/HRS 2008 Guidelines for Device-Based Therapy of Cardiac Rhythm Abnormalities. J. Am. Coll. Cardiol. 2008; 51; el-e62, 66 Pgs.

Fitbit Tracker, URL <http://www.fitbit.com/> (Web page cached on Sep. 10, 2008.).

Smith, Jawbone Up, URL <http://www.businessinsider.com/fitbit-flex-vs-jawbone-up-2013-5?op=1> (Jun. 1, 2013).

Kligfield, Paul et al., Recommendations for the Standardization and Interpretation of the Electrocardiogram: Part I. J.Am.Coll. Cardiol; 2007; 49; 1109-27, 75 Pgs.

Lauren Gravitz, "When Your Diet Needs a Band-Aid,"Technology Review, MIT. (May 1, 2009).

Lieberman, Jonathan, "How Telemedicine is Aiding Prompt ECG Diagnosis in Primary Care," British Journal of Community Nursing, vol. 13, No. 3, Mar. 1, 2008 (Mar. 1, 2008), pp. 123-126, XP009155082, ISSN: 1462-4753.

(56) References Cited

OTHER PUBLICATIONS

McManus et al., "A Novel Application for the Detection of an Irregular Pulse using an iPhone 4S in Patients with Atrial Fibrillation," vol. 10(3), pp. 315-319 (Mar. 2013.).
Nike+ Fuel Band, URL <http://www.nike.com/us/en_us/c/nikeplus-fuelband> (Web page cached on Jan. 11, 2013.).
P. Libby et al.,"Braunwald's Heart Disease—A Textbook of Cardiovascular Medicine," Chs. 11, pp. 125-148 and 12, pp. 149-193 (8th ed. 2008), American Heart Association.
Initial hands-on with Polar Loop activity tracker, URL <http://www.dcrainmaker.com/2013/09/polar-loop-firstlook.html> (Sep. 17, 2013).
Seifert, Dan, Samsung dives into fitness wearable with the Gear Fit/ The Verge, URL <http://www.theverge.com/2014/2/24/5440310/samsung-dives-into-fitness-wearables-with-the-gear-fit> (Feb. 24, 2014).
Soper, Taylor, Samsung's new Galaxy S5 flagship phone has fingerprint reader, heart rate monitor, URL <http://www.geekwire.com/2014/samsung-galaxy-s5-fingerprint> (Feb. 24, 2014).
Dolcourt, See the Samsung Galaxy S5's Heart rate monitor in action, URL <http://www.cnet.com/news/see-the-samsung-galaxy-s5s-heart-rate-monitor-in-action> (Feb. 25, 2014).
Sittig et al., "A Computer-Based Outpatient Clinical Referral System," International Journal of Medical Informatics, Shannon, IR, vol. 55, No. 2, Aug. 1, 1999, pp. 149-158, XO004262434, ISSN: 1386-5056(99)00027-1.
Sleepview, URL <http://www.clevemed.com/sleepview/overview.shtml> (Web page cached on Sep. 4, 2013.).
Actigraphy/ Circadian Rhythm SOMNOwatch, URL <http://www.somnomedics.eu/news-events/publications/somnowatchtm.html> (Web page cached on Jan. 23, 2010).
Zio Event Card, URL <http://www.irhythmtech.com/zio-solution/zio-event/> (Web page cached on Mar. 11, 2013.).
Zio Patch System, URL <http://www.irhythmtech.com/zio-solution/zio-system/index.html> (Web page cached on Sep. 8, 2013.).
Saadi et al. "Heart Rhythm Analysis Using ECG Recorded With a Novel Sternum Based Patch Technology—A Pilot Study." Cardiotechnix 2013—Proceedings of the International Congress on Cardiovascular Technologies, Sep. 20, 2013.
Anonymous. "Omegawave Launches Consumer App 2.0 in U.S. Endurance Sportswire—Endurance Sportswire." Jul. 11, 2013. URL:http://endurancesportswire.com/omegawave-launches-consumer-app-2-0-in-u-s/.
Chan et al. "Wireless Patch Sensor for Remote Monitoring of Heart Rate, Respiration, Activity, and Falls." pp. 6115-6118. 2013 35th Annual International Conference of the IEEE Engineering in Medical and Biology Society.
Wei et al. "A Stretchable and Flexible System for Skin-Mounted Measurement of Motion Tracking and Physiological Signals." pp. 5772-5775. 2014 36th Annual International Conference of the IEEE Engineering in Medicine and Biology Society. Aug. 26, 2014.
Daoud et al. "Fall Detection Using Shimmer Technology and Multiresolution Analysis." Aug. 2, 2013. URL: https://decibel.ni.com/content/docs/DOC-26652.
Libbus. "Adherent Cardiac Monitor With Wireless Fall Detection for Patients With Unexplained Syncope." Abstracts of the First AMA-IEEE Medical Technology Conference on Individualized Healthcare. May 22, 2010.
Duttweiler et al., "Probability Estimation in Arithmetic and Adaptive-Huffman Entropy Coders," IEEE Transactions on Image Processing. vol. 4, No. 3, Mar. 1, 1995, pp. 237-246.
Gupta et al., "An ECG Compression Technique for Telecardiology Application," India Conference (INDICON), 2011 Annual IEEE, Dec. 16, 2011, pp. 1-4.
Nave et al., "ECG Compression Using Long-Term Prediction," IEEE Transactions on Biomedical Engineering, IEEE Service Center, NY, USA, vol. 40, No. 9, Sep. 1, 1993, pp. 877-885.
Skretting et al., "Improved Huffman Coding Using Recursive Splitting," NORSIG, Jan. 1, 1999.
A Voss et al., "Linear and Nonlinear Methods for Analyses of Cardiovascular Variability in Bipolar Disorders," Bipolar Disorders, vol. 8, No. 5p. 1, Oct. 1, 2006, pp. 441-452, XP55273826, DK ISSN: 1398-5647, DOI: 10.1111/i.1399-5618.2006.00364.x.
Varicrad-Kardi Software User's Manual Rev. 1.1, Jul. 8, 2009 (Jul. 8, 2009), XP002757888, retrieved from the Internet: URL:http://www.ehrlich.tv/KARDiVAR-Software.pdf [retrieved on May 20, 2016].
Vedapulse UK, Jan. 1, 2014 (Jan. 1, 2014), XP002757887, Retrieved from the Internet: URL:http://www.vedapulseuk.com/diagnostic/ [retrieved on May 19, 2016].
http://www.originlab.com/origin#Data_Exploration 2015.
https://web.archive.org/web/20130831204020/http://www.biopac.com/research.asp?CatID=37&Main=Software (Aug. 2013).
http://www.gtec.at/Products/Software/g.BSanalyze-Specs-Features (2014).
Adinstruments:ECG Analysis Module for LabChart & PowerLab, 2008.
BIOPAC Systems, Inc. #AS148—Automated ECG Analysis , Mar. 24, 2006.
Health Research—Hexoskin Biometric Shirt | Hexoskin URL:http://www.hexoskin.com/pages/health-research (Web page cached on Dec. 2, 2014).
Jacob Kastrenakes, "Apple Watch uses four sensors to detect your pulse," Sep. 9, 2014. URL: http://www.theverge.com/2014/9/9/6126991/apple-watch-four-back-sensors-detect-activity.
Nicole Lee, "Samsung Gear S review: an ambitious and painfully flawed smartwatch," Dec. 1, 2014. URL: http://www.engadget.com/2014/12/01/samsung-gear-s-review/.
G. G. Ivanov, "HRV Analysis Under the Usage of Different Electrocardiopraphy Systems," Apr. 15, 2008 (Apr. 15, 2008), XP55511209, Retrieved from the Internet: URL:http://www.drkucera.eu/upload_doc/hrv_analysis_(methodical_recommendations).pdf [retrieved on Oct. 1, 2018].
Pranav Rajpurkar et al. "Cardiologist-Level Arrhythmia Detection with Convolutional Neural Networks,"arxiv.org, Cornell University Library, 201 Olin Library Cornell University Ithaca, NY 14853, Jul. 6, 2017 (Jul. 6, 2017), XP080774895.
Pourbabaee Bahareh et al. "Feature Learning with Deep Convolutional Neural Networks for Screening Patients with Paroxysmal Atrial Fibrillation," 2016 Neural Networks (IJCNN), 2016 International Joint Conference on Neural Networks (IJCNN), IEEE, Jul. 24, 2016 (Jul. 24, 2016), pp. 5057-5064, XP032992832, DOI: 10.1109/IJCNN.2016.7727866.
Xiong Zhaohan et al. "Robust ECG Signal Classification for Detection of Atrial Fibrillation Using a Novel Neural Network," 2017 Computing in Cardiology (CinC), CCAL, Sep. 24, 2017 (Sep. 24, 2017), pp. 1-4, XP033343575, DOI: 10.22489/CinC.2017.066-138.
Wallot et al., "Using Complexity Metrics With R-R Intervals and BPM Heart Rate Measures," Frontiers in Physiology, vol. 4, Article 211, pp. 1-8, Aug. 13, 2013. 2013.
https://www.meddeviceonline.com/doc/medtronic-launches-worlds-first-app-based-remote-monitoring-system-for-pacemakers-0001. Nov. 18, 2015.
https://fccid.io/LF524950/User-Manual/User-Manual-1944573 © Medtronic, Inc. 2012.
https://en.wikipedia.org/wiki/Convolutional_neural_network#Receptive_fields_in_the_visual_cortex (Year: 2017).
Dan Sapoznikov et al., "Comparison of Different Methodologies of Heart Rate Variability Analysis," Department of Cardiology, Hadassah University Hospital, P.O.B. 12000, Ein Kerem, Jerusalem 91120, Israel (1993).
Jeffrey J. Goldberger, MD, FHRS, et al., "Comparison of the Physiologic and Prognostic Implications of the Heart Rate Versus the RR Interval," Heart Rhythm, Elseview, US, vol. 11, No. 11, Jul. 30, 2014 (Jul. 30, 2014), pp. 1925-1933, XP029082764, ISSN: 1547-5271, DOI: 10.1016/J.HRTHM.2014.07.037 (2014).
Giuseppe Ciconte et al., "The Role of Implantable Cardiac Monitors in Artial Fibrillation Management," Journal for Atrial Finrillation: JAFIB, vol. 10, No. 2, Aug. 31, 2017 (Aug. 31, 2017), XP055732155, ISSN: 1941-6911, DOI: 10.4022/iafib. 1590. Aug. 31, 2017.
BioMonitor 2 Cardiac Monitor With Fast Insert Tools BIOTRONIK Home Monitoring, BioMonitor 2—technical manual, Jul. 6, 2017 (Jul. 6, 2017), pp. 1-29, XPO55732157, [retrieved on Sep. 18, 2020].

(56) References Cited

OTHER PUBLICATIONS

"RevealLINQ Product Specifications," Dec. 1, 2017 (Dec. 1, 2017), XPO55732158, [retrieved on Sep. 18, 2020].
Helmut Purerfellner et al.: "Miniaturized Reveal LINQ insertable cardiac monitoring system: First-in-human experience," Heart Rhythm, vol. 12. No. 6, Jun. 1, 2015 (Jun. 1, 2015), pp. 1113-1119, XP055732303, US ISSN: 1547-5271, DOI: 10.1016/j.hrthm. 2015.02.03.

\* cited by examiner

110

86

88

88

88

SUBCUTANEOUS P-WAVE CENTRIC INSERTABLE CARDIAC MONITOR WITH ENERGY HARVESTING CAPABILITIES

CROSS-REFERENCE TO RELATED APPLICATION

This non-provisional patent application claims priority under 35 U.S.C. § 119(e) to U.S. Provisional Patent application, Ser. No. 62/870,506, filed Jul. 3, 2019, the disclosure of which is incorporated by reference.

FIELD

This application relates in general to electrocardiographic monitoring and, in particular, to a subcutaneous P-wave-centric insertable cardiac monitor (ICM) with internal energy harvesting capabilities.

BACKGROUND

The electrocardiogram (ECG) was invented by a Dutch physiologist, Willem Einthoven, in 1903. Physicians have since used ECGs to diagnose heart problems and other medical concerns. The medical and engineering principles underlying Einthoven's work are still applicable today, and although ECG machines have evolved to a broad array of different systems, over the past century, the fundamental role of an ECG machine remains the same: to record from the skin surface transmembrane ionic currents that are generated within the heart during cardiac activation and recovery.

Cardiac depolarization, which is the spread of electrical current throughout the heart, originates in the sinoatrial (SA) node in the right atrium and spreads leftward towards the left atrium and inferiorly towards the atrioventricular (AV) node. Thereafter a delay, occasioned by the AV node, allows atrial blood to enter the ventricles, prior to the continuation of the depolarization current proceeding down the Bundle of His and into the right and left bundle branches, then advancing to the Purkinje fibers, and finally spreading to activate the right and left ventricular muscle fibers themselves that lead to the heart muscle squeezing the blood supply forward.

During each cardiac cycle, the transmembrane ionic currents create an electrical field in and around the heart that can be detected by ECG electrodes either placed on the skin or implanted under the skin of the thorax to record far field electrical signals from the heart. These far field electrical signals are the captured ECG signals that can be visually depicted in an ECG trace as the PQRSTU waveforms, each letter of which represents a specific electrical activity in the heart well known to cardiologists. Within each cardiac cycle, these waveforms indicate key aspects of cardiac electrical activity. The critical P-wave component of each heartbeat represents atrial electrical activity, the electrical signal that is essential if one is to understand heart rhythm disorders. The QRS components represent ventricular electrical activity, equally critical to understanding heart rhythm disorders. The TU components represent ventricular cell voltages that are the result of resetting cellular currents in preparation for the next cardiac cycle. The TU components are generally of limited value for the purposes of understanding heart rhythm disorders and are rarely addressed in the analysis of heart rhythm disorders per se. (Note that the signals involved in the resetting of the atria are so minuscule as to not be visible in an ECG trace or, even in a standard intra-cardiac recording.)

Practically, the QRS components of the ventricle electrical activity are often termed the "R-wave," in brief, as a shorthand way of identifying ventricular electrical activity in its entirety. (Henceforth, the shorthand version of "R-wave" will be used to indicate ventricular activity and "P-wave" will be used to indicate atrial activity.) These "waves" represent the two critical components of arrhythmia monitoring and diagnosis performed every day hundreds of thousands of times across the United States. Without a knowledge of the relationship of these two basic symbols, heart rhythm disorders cannot be reliably diagnosed. Visualizing both the P-wave and the R-wave allow for the specific identification of a variety of atrial tachyarrhythmias (also known as supraventricular tachyarrhythmias, or SVTs), ventricular tachyarrhythmias (VTs), and bradycardias related to sinus node and atrioventricular (AV) node dysfunction. These categories are well understood by cardiologists but only accurately diagnosable if the P-wave and the R-wave are visualized and their relationship and behavior are clear. Visualization of the R-wave is usually readily achievable, as the R-wave is a high voltage, high frequency signal easily recorded from the skin's surface. However, as the ECG bipole spacing and electrode surface area decreases, even the R-wave can be a challenge to visualize. To make matters of rhythm identification more complicated, surface P-waves can be much more difficult to visualize from the surface because of their much lower voltage and signal frequency content. P-wave visualization becomes exacerbated further when the recording bipole inter-electrode spacing decreases.

Subcutaneous ECG monitors, because of their small size, have greater problems of demonstrating a clear and dependable P-wave. The issues related to a tiny atrial voltage are exacerbated by the small size of insertable cardiac monitors (ICMs), the signal processing limits imposed upon them by virtue of their reduced electrode size, and restricted inter-electrode spacing. Conventional subcutaneous ICMs, as well as most conventional surface ECG monitors, are notorious for poor visualization of the P-wave, which remains the primary reason that heart rhythm disorders cannot precisely be identified today from ICMs. Furthermore, even when physiologically present, the P-wave may not actually appear on an ECG because the P-wave's visibility is strongly dependent upon the signal capturing ability of the ECG recording device's sensing circuitry. This situation is further influenced by several factors, including electrode configuration, electrode surface areas and shapes, inter-electrode spacing; where the electrodes are placed on or within the body relative to the heart's atria. Further, the presence or absence of ambient noise and the means to limit the ambient noise is a key aspect of whether the low amplitude atrial signal can be seen.

Conventional ICMs are generally capable of monitoring a patient's heart rhythm for up to three years and are often used after diagnostic measures when dermal ECG monitors fail to identify a suspected arrhythmia. Consequently, when a physician is strongly suspicious of a serious cardiac rhythm disorder that may have caused loss of consciousness or stroke, for example, the physician will often proceed to the insertion of an ICM under the skin of the thorax. Although traditionally, the quality of the signal is limited with ICMs with respect to identifying the P-wave, the duration of monitoring is hoped to compensate for poor P-wave recording. This situation has led to a dependence on scrutiny of R-wave behavior, such as RR interval (R-wave-to-R-wave interval) behavior, often used as a surrogate for diagnosing atrial fibrillation, a potential cause of stroke. To a limited extent, this approach has some degree of value. Nevertheless, better recording of the P-wave would result in a significant diagnostic improvement, not only in the case of atrial fibrillation, but in a host of other rhythm disorders that can result in syncope or loss of consciousness, like VT or heart block.

The P-wave is the most difficult ECG signal to capture by virtue of originating in the low tissue mass atria and having both low voltage amplitude and relatively low frequency content. Notwithstanding these physiological constraints, ICMs are popular, albeit limited in their diagnostic yield. The few ICMs that are commercially available today, including the Reveal LINQ ICM, manufactured by Medtronic, Inc., Minneapolis, Minn., the BioMonitor 2 (AF and S versions), manufactured by Biotronik SE & Co. KG, Berlin, Germany, and the Abbott Confirm Rx ICM, manufactured by Abbott Laboratories, Chicago, Ill., all are uniformly limited in their abilities to clearly and consistently sense, record, and deliver the P-wave.

Typically, the current realm of ICM devices use a loop recorder where cumulative ECG data lasting for around an hour is continually overwritten unless an episode of pre-programmed interest occurs or a patient marker is manually triggered. The limited temporal window afforded by the recordation loop is yet another restriction on the evaluation of the P-wave, and related cardiac morphologies, and further compromises diagnostic opportunities.

For instance, Medtronic's Reveal LINQ ICM delivers long-term subcutaneous ECG monitoring for up to three years, depending on programming. The monitor is able to store up to 59 minutes of ECG data, include up to 30 minutes of patient-activated episodes, 27 minutes of automatically detected episodes, and two minutes of the longest atrial fibrillation (AF) episode stored since the last interrogation of the device. The focus of the device is more directed to recording duration and programming options for recording time and patient interactions rather than signal fidelity. The Reveal LINQ ICM is intended for general purpose ECG monitoring and lacks an engineering focus on P-wave visualization. Moreover, the device's recording circuitry is intended to secure the ventricular signal by capturing the R-wave, and is designed to accommodate placement over a broad range of subcutaneous implantation sites, which is usually sufficient if one is focused on the R-wave given its amplitude and frequency content, but of limited value in capturing the low-amplitude, low-frequency content P-wave. Finally, electrode spacing, surface areas, and shapes are dictated (and limited) by the physical size of the monitor's housing which is quite small, an aesthetic choice, but unrealistic with respect to capturing the P-wave.

Similar in design is the titanium housing of Biotronik's BioMonitor 2 but with a flexible silicone antenna to mount a distal electrode lead, albeit of a standardized length. This standardized length mollifies, in one parameter only, the concerns of limited inter-electrode spacing and its curbing effect on securing the P-wave. None of the other factors related to P-wave signal revelation are addressed. Therefore the quality of sensed P-waves reflects a compromise caused by closely-spaced poles that fail to consistently preserve P-wave fidelity, with the reality of the physics imposed problems of signal-to-noise ratio limitations remaining mostly unaddressed.

Further, the physical size of existing implantable monitors limits the size of a power source present in those monitors, which in turn limits a duration of a monitoring possible without a surgical intervention to replace the power source in the monitoring. For a patient whose condition requires extended, potentially periodic life-long monitoring, the existing implantable monitors are of a limited usefulness, subjecting them to surgical intervention and possible associated complications when the power supply of such an implantable monitor runs out. Further, the limitations of the power supply impact how often and how much the implantable monitor offloads collected data due to a large power consumption associated with the wireless transmission.

Therefore, a need remains for a continuously recording long-term ICM particularly attuned to capturing low amplitude cardiac action potential propagation from the atria, that is, the P-wave, for accurate arrhythmia event capture and subsequent diagnosis, as well as capable of a prolonged monitoring and frequent data offload without needing a surgical intervention to replace the power source within the ICM.

SUMMARY

Long-term electrocardiographic and physiological monitoring over a period lasting up to several years in duration can be provided through a continuously-recording subcutaneous insertable cardiac monitor (ICM). The sensing circuitry and the physical layout of the electrodes are specifically optimized to capture electrical signals from the propagation of low amplitude, relatively low frequency content cardiac action potentials, particularly the P-waves that are generated during atrial activation. In general, the ICM is intended to be implanted centrally and positioned axially and slightly to either the left or right of the sternal midline in the parasternal region of the chest.

The length of the monitoring is extended, potentially for a life time of the patient, by including an internal energy harvesting module in the ICM. The energy harvesting module harvests energy from outside the ICM, and provides the harvested energy for powering the circuitry of the ICM, either directly or by recharging a power cell within the ICM. As the circuitry of the ICM requires a low amount of electrical power, the harvested energy can be sufficient to support the functioning of the ICM 12 even when the electrical power stored on the ICM at the time of implantation runs out. The presence of the energy harvesting module further allows for a frequent wireless transmission of a large amount of collected data.

In one embodiment, a P-wave centric subcutaneous insertable cardiac monitor (ICM) with internal energy harvesting capabilities is provided. The ICM includes an implantable housing made off a biocompatible material that is suitable for implantation within a living body; at least one pair of ECG sensing electrodes provided on a ventral surface and on opposite ends of the implantable housing operatively placed to facilitate sensing in closest proximity to the low amplitude, low frequency content cardiac action potentials that are generated during atrial activation; electronic circuitry provided within the housing assembly comprising a low power microcontroller operable to execute under modular micro program control as specified in firmware, an ECG front end circuit interfaced to the microcontroller and configured to capture the cardiac action potentials sensed by the pair of ECG sensing electrodes which are output as ECG signals, and non-volatile memory electrically interfaced with the microcontroller and operable to continuously store samples of the ECG signals; and an energy harvesting module electrically interfaced to the electronic circuitry and configured to generate electrical energy based on input from an environment outside of the implantable housing when the implantable housing is implanted into the living body, wherein at least a portion of generated electrical energy is used by the electronic circuitry.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

BRIEF DESCRIPTIONS OF DRAWINGS

DETAIL DESCRIPTION

Figure 1:
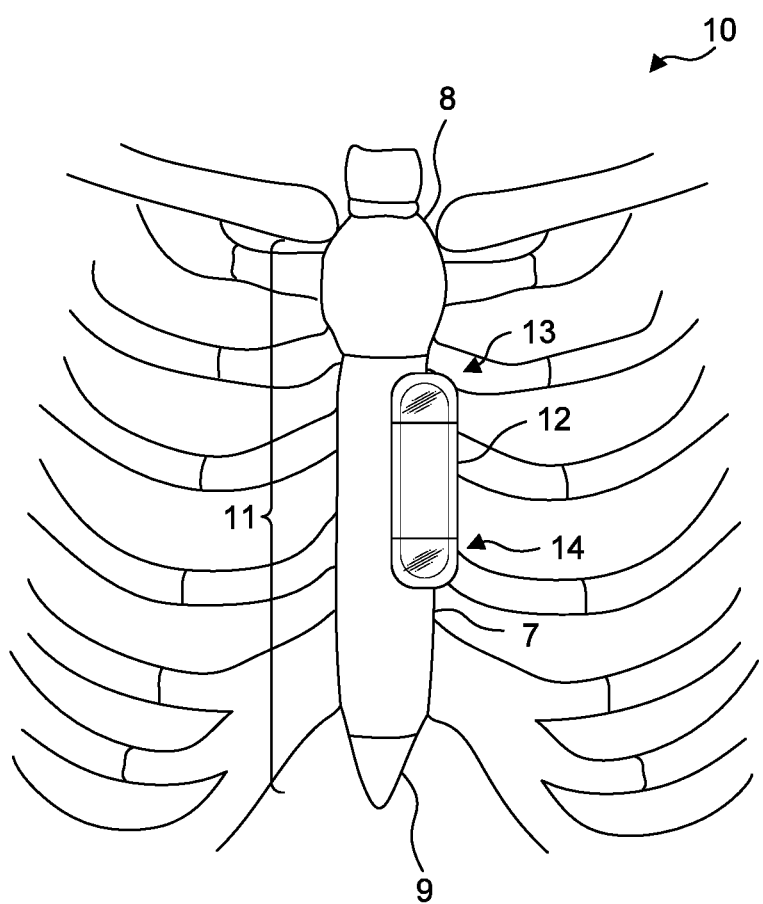
FIG. 1 is a diagram showing, by way of example, a subcutaneous P-wave centric insertable cardiac monitor (ICM) for long term electrocardiographic monitoring in accordance with one embodiment.

Long-term electrocardiographic and physiological monitoring over a period lasting up to several years in duration can be provided through a continuously-recording subcutaneous insertable cardiac monitor (ICM). FIG. 1 is a diagram showing, by way of example, a subcutaneous P-wave centric ICM 12 for long term electrocardiographic monitoring in accordance with one embodiment. The ICM 12 is implanted in the parasternal region 11 of a patient 10. The sensing circuitry and components, compression algorithms, and the physical layout of the electrodes are specifically optimized to capture electrical signals from the propagation of low amplitude, relatively low frequency content cardiac action potentials, particularly the P-waves generated during atrial activation. The position and placement of the ICM 12 coupled to engineering considerations that optimize the ICM's sensing circuitry, discussed infra, aid in demonstrating the P-wave clearly.

Implantation of a P-wave centric ICM 12 in the proper subcutaneous site facilitates the recording of high quality ECG data with a good delineation of the P-wave. In general, the ICM 12 is intended to be implanted anteriorly and be positioned axially and slightly to either the right or left of the sternal midline in the parasternal region 11 of the chest, or if sufficient subcutaneous fat exists, directly over the sternum. Optimally, the ICM 12 is implanted in a location left parasternally to bridge the left atrial appendage. However, either location to the right or left of the sternal midline is acceptable; placement of the device, if possible, should bridge the vertical height of the heart, which lies underneath the sternum 7, thereby placing the ICM 12 in close proximity to the anterior right atrium and the left atrial appendage that lie immediately beneath.

The ICM 12 is shaped to fit comfortably within the body under the skin and to conform to the contours of the patient's parasternal region 11 when implanted immediately to either side of the sternum 7, but could be implanted in other locations of the body. In most adults, the proximal end 13 of the ICM 12 is generally positioned below the manubrium 8 but, depending upon patient's vertical build, the ICM 12 may actually straddle the region over the manubrium 8. The distal end 14 of the ICM 12 generally extends towards the xiphoid process 9 and lower sternum but, depending upon the patient's build, may actually straddle the region over or under the xiphoid process 9, lower sternum and upper abdomen.

Although internal tissues, body structures, and tissue boundaries can adversely affect the current strength and signal fidelity of all body surface potentials, subsurface low amplitude cardiac action potentials, particularly P-wave signals with a normative amplitude of less than 0.25 millivolts (mV) and a normative duration of less than 120 milliseconds (ms), are most apt to be negatively impacted by these factors. The atria, which generate the P wave, are mostly located posteriorly within the thoracic cavity (with the exception of the anterior right atrium, right atrial appendage and left atrial appendage). The majority of the left atrium constitutes the portion of the heart furthest away from the surface of the skin on the chest and harbors the atrial tissue most likely to be the source of serious arrhythmias, like atrial fibrillation. Conversely, the ventricles, which generate larger amplitude signals, are located anteriorly as in the case of the anterior right ventricle and most of the anterior left ventricle situated relatively close to the skin surface of the central and left anterior chest. These factors, together with larger size and more powerful impulse generation from the ventricles, contribute to the relatively larger amplitudes of ventricular waveforms.

Nevertheless, as explained supra, both the P-wave and the R-wave are required for the physician to make a proper rhythm diagnosis from the dozens of arrhythmias that can occur. Yet, the quality of P-waves is more susceptible to weakening from distance and the intervening tissues and structures and from signal attenuation and signal processing than the high voltage waveforms associated with ventricular activation. The added value of avoiding further signal attenuation resulting from dermal impedance makes a subcutaneous P-wave centric ICM even more likely to match, or even outperform dermal ambulatory monitors designed to analogous engineering considerations and using similar sensing circuitry and components, compression algorithms, and physical layout of electrodes, such as described in U.S. Pat. No. 9,545,204, issued Jan. 17, 2017 to Bishay et al.; U.S. Pat. No. 9,730,593, issued Aug. 15, 2017 to Felix et al.; U.S. Pat. No. 9,700,227, issued Jul. 11, 2017 to Bishay et al.; U.S. Pat. No. 9,717,433, issued Aug. 1, 2017 to Felix et al.; and U.S. Pat. No. 9,615,763, issued Apr. 11, 2017 to Felix et al., the disclosures of which are incorporated by reference.

The ICM 12 can be implanted in the patient's chest using, for instance, a minimally invasive subcutaneous implantation instrument or other suitable surgical implement. The ICM 12 is positioned slightly to the right or left of midline, covering the center third of the chest, roughly between the second and sixth ribs, approximately spanning between the level of the manubrium 8 and the level of the xiphoid process 9 on the inferior border of the sternum 7, depending upon the vertical build of the patient 10.

During monitoring, the amplitude and strength of action potentials sensed by an ECG devices, including dermal ECG monitors and ICMs, can be affected to varying degrees by cardiac, cellular, extracellular, vector of current flow, and physical factors, like obesity, dermatitis, lung disease, large breasts, and high impedance skin, as can occur in dark-skinned individuals. Performing ECG sensing subcutaneously in the parasternal region 11 significantly improves the ability of the ICM 12 to counter some of the effects of these factors, particularly high skin impedance and impedance from subcutaneous fat. Thus, the ICM 12 exhibits superior performance when compared to conventional dermal ECG monitors to existing implantable loop recorders, ICMs, and other forms of implantable monitoring devices by virtue of its engineering and proven P-wave documentation above the skin, as discussed in W. M. Smith et al., "Comparison of diagnostic value using a small, single channel, P-wave centric sternal ECG monitoring patch with a standard 3-lead Holter system over 24 hours," Am. Heart J., March 2017; 185:67-73, the disclosure of which is incorporated by reference.

Moreover, the sternal midline implantation location in the parasternal region 11 allows the ICM's electrodes to record an ECG of optimal signal quality from a location immediately above the strongest signal-generating aspects of the atrial. Signal quality is improved further in part because cardiac action potential propagation travels simultaneously along a north-to-south and right-to-left vector, beginning high in the right atrium and ultimately ending in the posterior and lateral region of the left ventricle. Cardiac depolarization originates high in the right atrium in the SA node before concurrently spreading leftward towards the left atrium and inferiorly towards the atrioventricular (AV) node. On the proximal end 13, the ECG electrodes of the ICM 12 are subcutaneously positioned with the upper or superior pole (ECG electrode) slightly to the right or left of the sternal midline in the region of the manubrium 8 and, on the distal end 14, the lower or inferior pole (ECG electrode) is similarly situated slightly to the right or left of the sternal midline in the region of the xiphoid process 9 and lower sternum 7. The ECG electrodes of the ICM 12 are placed primarily in a north-to-south orientation along the sternum 7 that corresponds to the north-to-south waveform vector exhibited during atrial activation. This orientation corresponds to the aVF lead used in a conventional 12-lead ECG that is used to sense positive or upright P-waves. In addition, the electrode spacing and the electrodes' shapes and surface areas mimic the electrodes used in the ICM's dermal cousin, designed as part of the optimal P-wave sensing electrode configuration, such as provided with the dermal ambulatory monitors cited supra.

Figure 2:
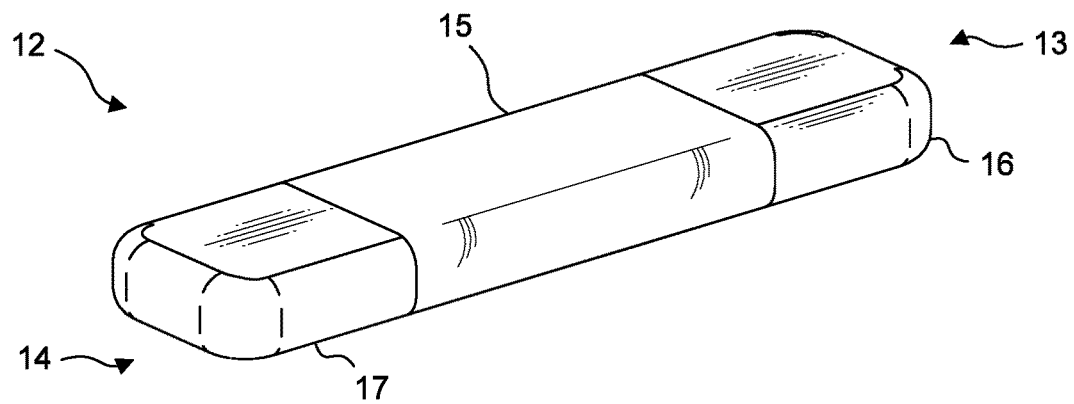
FIGS. 2 and 3 are respectively top and bottom perspective views showing the ICM of FIG. 1.
Figure 3:
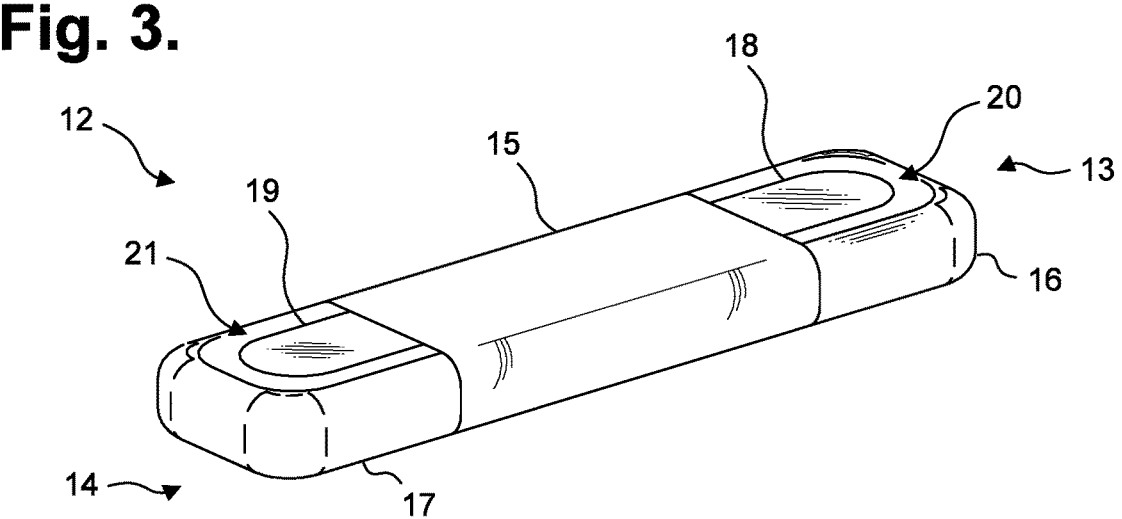

Despite the challenges faced in capturing low amplitude cardiac action potentials, the ICM 12 is able to operate effectively using only two electrodes that are strategically sized and placed in locations ideally suited to high fidelity P-wave signal acquisition. This approach has been shown to clinically outperform more typical multi-lead monitors because of the improved P-wave clarity, as discussed in W. M. Smith et al., cited supra. FIGS. 2 and 3 are respectively top and bottom perspective views showing the ICM 12 of FIG. 1. Physically, the ICM 12 is constructed with a hermetically sealed implantable housing 15 with at least one ECG electrode forming a superior pole on the proximal end 13 and at least one ECG electrode forming an inferior pole on the distal end 14.

When implanted, the housing 15 is oriented most cephalad. The housing 15 is constructed of titanium, stainless steel or other biocompatible material. The housing 15 contains the sensing, recordation and interfacing circuitry of the ICM 12, plus a long life battery. A wireless antenna is integrated into or within the housing 15 and can be positioned to wrap around the housing's internal periphery or location suited to signal reception. Other wireless antenna placement or integrations are possible, as further described below with reference to FIG. 18.

Physically, the ICM 12 has four ECG electrodes 16, 17, 18, 19. There could also be additional ECG electrodes, as discussed infra. The ECG electrodes include two ventral (or dorsal) ECG electrodes 18, 19 and two wraparound ECG electrodes 16, 17. One ventral ECG electrode 18 is formed on the proximal end 13 and one ventral ECG electrode 19 is formed on the distal end 14. One wraparound ECG electrode 16 is formed circumferentially about the proximal end 13 and one wraparound ECG electrode 17 is formed circumferentially about the distal end 14. Each wraparound ECG electrode 16, 17 is electrically insulated from its respective ventral ECG electrode 18, 19 by a periphery 20, 21.

The four ECG electrodes 16, 17, 18, 19 are programmatically controlled by a microcontroller through onboard firmware programming to enable a physician to choose from several different electrode configurations that vary the electrode surface areas, shapes, and inter-electrode spacing. The sensing circuitry can be programmed, either pre-implant or in situ, to use different combinations of the available ECG electrodes (and thereby changing electrode surface areas, shapes, and inter-electrode spacing), including pairing the two ventral ECG electrodes 16, 17, the two wraparound ECG electrodes 18, 19, or one ventral ECG electrode 16, 17 with one wraparound ECG electrode 18, 19 located on the opposite end of the housing 15. In addition, the periphery 20, 21 can be programmatically controlled to logically combine the wraparound ECG electrode 16, 17 on one end of the ICM 12 with its corresponding ventral ECG electrode 18, 19 to form a single virtual ECG electrode with larger surface area and shape. (Although electronically possible, the two ECG electrodes that are only on one end of the ICM 12, for instance, wraparound ECG electrode 16 and ventral ECG electrode 18, could be paired; however, the minimal interelectrode spacing would likely yield a signal of poor fidelity in most situations.)

In a further embodiment, the housing 15 and contained circuitry can be provided as a standalone ICM core assembly to which a pair of compatible ECG electrodes can be operatively coupled to form a full implantable ICM device.

Figure 4:
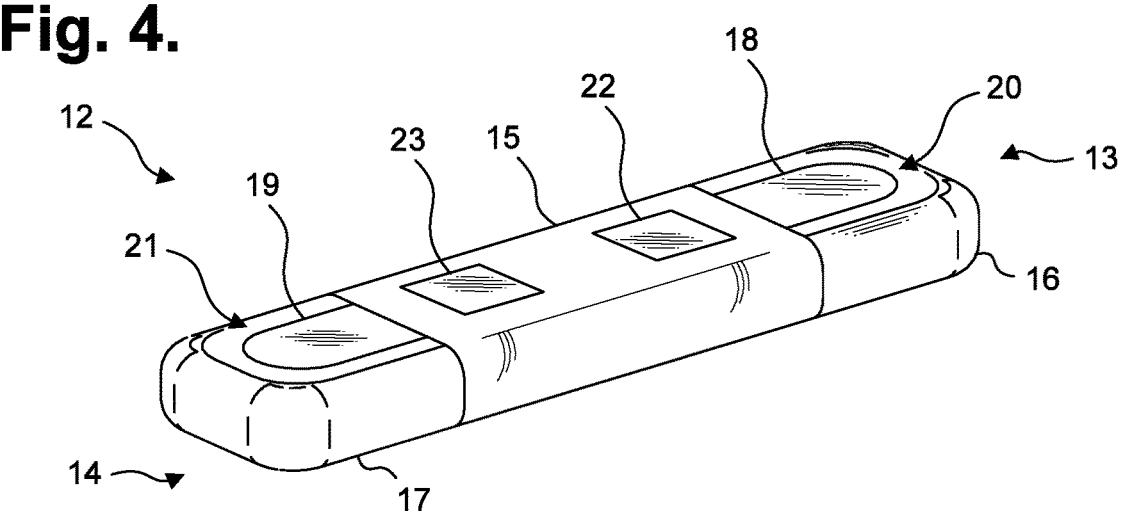
FIG. 4 is a bottom perspective view showing the ICM of FIG. 1 in accordance with a further embodiment.

Other ECG electrode configurations are possible. For instance, additional ECG electrodes can be provided to increase the number of possible electrode configurations, all of which are to ensure better P-wave resolution. FIG. 4 is a bottom perspective view showing the ICM 12 of FIG. 1 in accordance with a further embodiment. An additional pair of ventral ECG electrodes 22, 23 are included on the housing's ventral surface. These ventral ECG electrodes 22, 23 are spaced closer together than the ventral ECG electrodes 18, 19 on the ends of the housing 15 and a physician can thus choose to pair the two inner ventral ECG electrodes 22, 23 by themselves to allow for minimal electrode-to-electrode spacing, or with the other ECG electrodes 16, 17, 18, 19 to vary electrode surface areas, shapes, and inter-electrode spacing even further to explore optimal configurations to acquire the P-wave.

Figure 5:
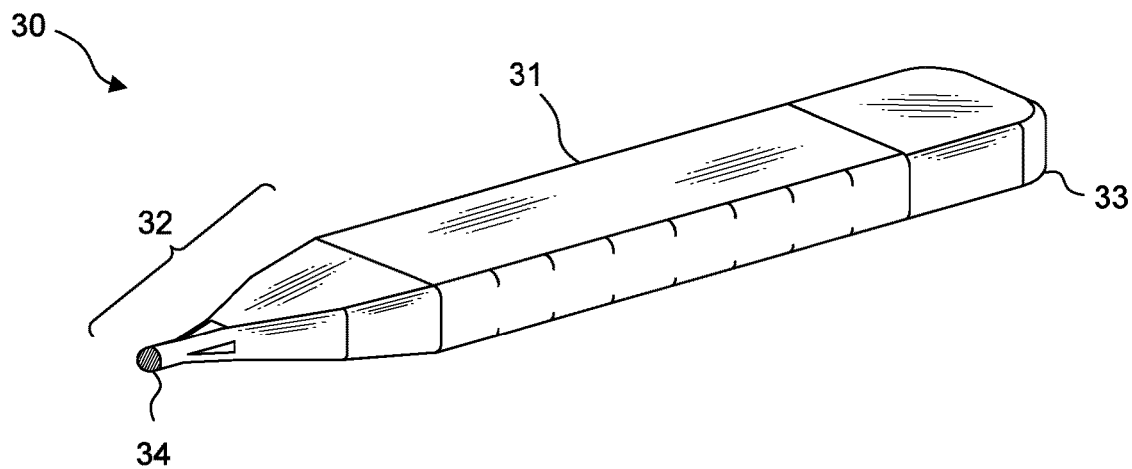
FIGS. 5 and 6 are respectively top and bottom perspective views showing an ICM in accordance with a still further embodiment.
Figure 6:
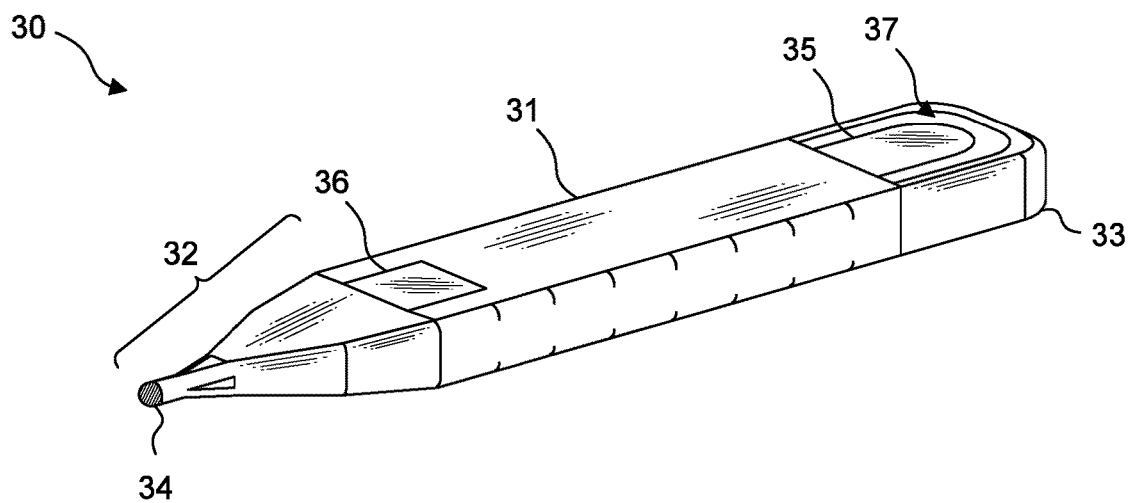

Other housing configurations of the ICM are possible. For instance, the housing of the ICM can be structured to enhance long term comfort and fitment, and to accommodate a larger long life battery or more circuitry or features, including physiologic sensors, to provide additional functionality. FIGS. 5 and 6 are respectively top and bottom perspective views showing an ICM 30 in accordance with a still further embodiment. The ICM 30 has a housing 31 with a tapered extension 32 that is terminated on the distal end with an electrode 34. On a proximal end, the housing 31 includes a pair of ECG electrodes electrically insulated by a periphery 37 that include a ventral ECG electrode 33 and a wraparound ECG electrode 34. In addition, a ventral ECG electrode 36 is oriented on the housing's distal end before the tapered extension 32. Still other housing structures and electrode configurations are possible.

In general, the basic electrode layout is sufficient to sense cardiac action potentials in a wide range of patients. Differences in thoracic tissue density and skeletal structure from patient to patient, though, can affect the ability of the sensing electrodes to efficaciously capture action potential signals, yet the degree to which signal acquisition is affected may not be apparent until after an ICM has been implanted and deployed, when the impacts of the patient's physical constitution and his patterns of mobility and physical movement on ICM monitoring can be fully assessed.

Figure 7:
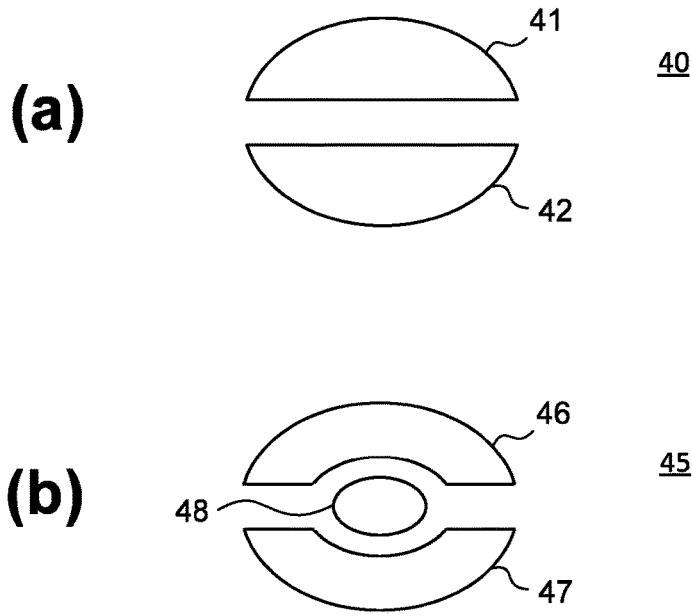
FIG. 7 is a plan view showing further electrode configurations.

In further embodiments, the electrodes can be configured post-implant to allow the ICM to better adapt to a particular patient's physiology. For instance, electrode configurations having more than two sensing electrodes are possible. FIG. 7 is a plan view showing further electrode configurations. Referring first to FIG. 7(a), a single disc ECG electrode 40 could be bifurcated to form a pair of half-circle ECG electrodes 41, 42 that could be programmatically selected or combined to accommodate a particular patients ECG signal characteristics post-ICM implant. Referring next to FIG. 7(b), a single disc ECG electrode 45 could be divided into three sections, a pair of crescent-shaped ECG electrodes 46, 47 surrounding a central semicircular ECG electrode 48 that could similarly be programmatically selected or combined. Still other ECG electrode configurations are possible.

Figure 8:
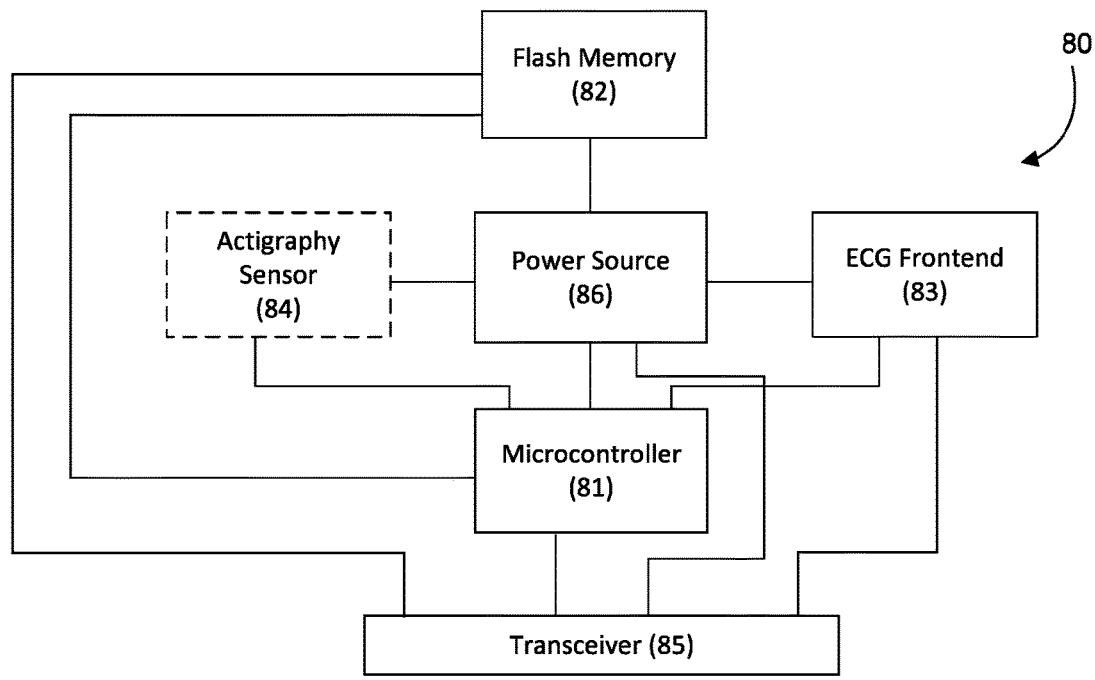
FIG. 8 is a functional block diagram showing the P-wave focused component architecture of the circuitry of the ICM of FIG. 1.

ECG monitoring and other functions performed by the ICM 12 are provided through a micro controlled architecture. FIG. 8 is a functional block diagram showing the P-wave focused component architecture of the circuitry 80 of the ICM 12 of FIG. 1. The circuitry 80 is powered through the long life battery 21 provided in the housing 15. Operation of the circuitry 80 of the ICM 12 is managed by a microcontroller 81, such as the EFM32 Tiny Gecko 32-bit microcontroller, manufactured by Silicon Laboratories Inc., Austin, Tex. The microcontroller 81 has flexible energy management modes and includes a direct memory access controller and built-in analog-to-digital and digital-to-analog converters (ADC and DAC, respectively). The microcontroller 81 also includes a program memory unit containing internal flash memory (not shown) that is readable, writeable, and externally programmable.

The microcontroller 81 operates under modular micro program control as specified in firmware stored in the internal flash memory. The functionality and firmware modules relating to signal processing by the microcontroller 81 are further described infra with reference to FIG. 11. The microcontroller 81 draws power from the battery provided in the housing 15 and connects to the ECG front end circuit 83. In a further embodiment, the front end circuit 83 measures raw dermal electrical signals using a driven reference signal that eliminates common mode noise, as further described infra.

The circuitry 80 of the ICM 12 also includes a flash memory 82 external to the microcontroller 81, which the microcontroller 81 uses for continuously storing samples of ECG monitoring signal data and other physiology, such as respiratory rate, blood oxygen saturation level ($SpO_2$), blood pressure, temperature sensor, and physical activity, and device and related information. The flash memory 82 also draws power from the battery provided in the housing 15. Data is stored in a serial flash memory circuit, which supports read, erase and program operations over a communications bus. The flash memory 82 enables the microcontroller 81 to store digitized ECG data. The communications bus further enables the flash memory 82 to be directly accessed wirelessly through a transceiver 85 coupled to an antenna 17 built into (or provided with) the housing 15, as further described infra with reference to FIG. 9. The transceiver 85 can be used for wirelessly interfacing over Bluetooth or other types of wireless technologies for exchanging data over a short distance with a paired mobile device, including smartphones and smart watches, that are designed to communicate over a public communications infrastructure, such as a cellular communications network, and, in a further embodiment, other wearable (or implantable) physiology monitors, such as activity trackers worn on the wrist or body. Other types of device pairings are possible, including with a desktop computer or purpose-built bedside monitor. The transceiver 85 can be used to offload stored ECG monitoring data and other physiology data and information and for device firmware reprogramming. In a further embodiment, the flash memory 82 can be accessed through an inductive coupling (not shown).

Figure 11:
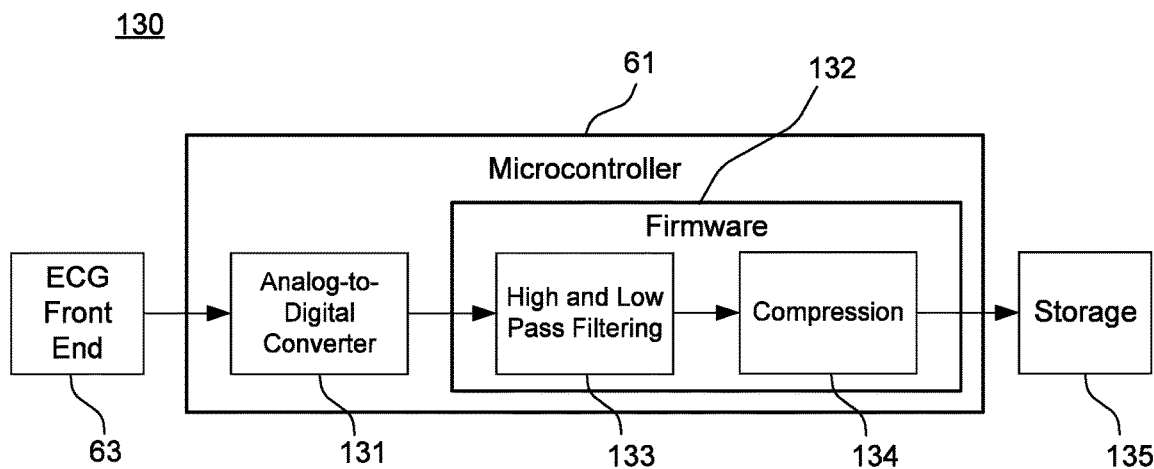
FIG. 11 is a functional block diagram showing the signal processing functionality of the microcontroller.

The microcontroller 81 includes functionality that enables the acquisition of samples of analog ECG signals, which are converted into a digital representation, as further described infra with reference to FIG. 11. In one mode, the microcontroller 81 implements a loop recorder feature that will acquire, sample, digitize, signal process, and store digitized ECG data into available storage locations in the flash memory 82 until all memory storage locations are filled, after which existing stored digitized ECG data will either be overwritten through a sliding window protocol, albeit at the cost of potentially losing the stored data that was overwritten, if not previously downloaded, or transmitted wirelessly to an external receiver to unburden the flash memory. In another mode, the stored digitized ECG data can be maintained permanently until downloaded or erased to restore memory capacity. Data download or erasure can also occur before all storage locations are filled, which would free up memory space sooner, albeit at the cost of possibly interrupting monitoring while downloading or erasure is performed. Still other modes of data storage and capacity recovery are possible.

The circuitry 80 of the ICM 12 can include functionality to programmatically select pairings of sensing electrodes when the ICM 12 is furnished with three or more electrodes. In a further embodiment, multiple sensing electrodes could be provided on the ICM 12 to provide a physician the option of fine-tuning the sensing dipole (or tripole or multipole) in situ by parking active electrodes and designating any remaining electrodes inert. The pairing selection can be made remotely through an inductive coupling or by the transceiver 85 via, for instance, a paired mobile device, as further described infra. Thus, the sensing electrode configuration, including number of electrodes, electrode-to-electrode spacing, and electrode size, shape, surface area, and placement, can be modified at any time during the implantation of the ICM 12.

In a further embodiment, the circuitry 80 of the ICM 12 can include an actigraphy sensor 84 implemented as a 3-axis accelerometer. The accelerometer may be configured to generate interrupt signals to the microcontroller 81 by independent initial wake up and free fall events, as well as by device position. In addition, the actigraphy provided by the accelerometer can be used during post-monitoring analysis to correct the orientation of the ICM 12 if, for instance, the ICM 12 has been inadvertently implanted upside down, that is, with the ICM's housing oriented caudally, as well as for other event occurrence analyses.

In a still further embodiment, the circuitry 80 of the ICM 12 can include one or more physiology sensors. For instance, a physiology sensor can be provided as part of the circuitry 80 of the ICM 12, or can be provided on the electrode assembly 14 with communication with the microcontroller 81 provided through a circuit trace. The physiology sensor can include an $SpO_2$ sensor, blood pressure sensor, temperature sensor, respiratory rate sensor, glucose sensor, airflow sensor, volumetric pressure sensing, or other types of sensor or telemetric input sources.

In a yet further embodiment, firmware with programming instructions, including machine learning and other forms of artificial intelligence-originated instructions, can be downloaded into the microcontroller's internal flash memory. The firmware can include heuristics to signal patient and physician with alerts over health conditions or arrhythmias of selected medical concern, such as where a heart pattern particular to the patient is identified and the ICM 12 is thereby reprogrammed to watch for a reoccurrence of that pattern, after which an alert will be generated and sent to the physician (or other caregiver) through the transceiver 85 via, for instance, a paired mobile device. Similarly, the firmware can include heuristics that can be downloaded to the ICM 12 to actively identify or narrow down a pattern (or even the underlying cause) of sporadic cardiac conditions, for instance, atrial tachycardia (AT), atrial fibrillation (AF), atrial flutter (AFL), AV node reciprocating tachycardia, ventricular tachycardia (VT), sinus bradycardia, asystole, complete heart block, and other cardiac arrhythmias, again, after which an alert will be generated and sent to the physician (or other caregiver) through the transceiver 85. For instance, an alert that includes a compressed ECG digitized sample can also be wirelessly transmitted by the ICM 12 upon the triggering of a preset condition, such as an abnormally low heart rate in excess of 170 beats per minute (bpm), an abnormally low heart rate falling below 30 bpm, or AF detected by onboard analysis of RR interval variability by the microcontroller 61. Finally, a similar methodology of creating firmware programming tailored to the monitoring and medical diagnostic needs of a specific patient (or patient group or general population) can be used for other conditions or symptoms, such as syncope, palpitations, dizziness and giddiness, unspecified convulsions, abnormal ECG, transient cerebral ischemic attacks and related syndromes, cerebral infarction, occlusion and stenosis of pre-cerebral and cerebral arteries not resulting in cerebral infarction personal history of transient ischemic attack, and cerebral infarction without residual deficits, to trigger an alert and involve the physician or initiate automated analysis and follow up back at the patient's clinic. Finally, in a still further embodiment, the circuitry 80 of the ICM 12 can accommodate patient-interfaceable components, including an external tactile feedback device (not shown) that wirelessly interfaces to the ICM 12 through the transceiver 85. A patient 10 can press the external tactile feedback device to mark events, such as a syncope episode, or to perform other functions. The circuitry 80 can also accommodate triggering an external buzzer 67, such as a speaker, magnetic resonator or piezoelectric buzzer, implemented as part of the external tactile feedback device or as a separate wirelessly-interfaceable component. The buzzer 67 can be used by the microcontroller 81 to indirectly output feedback to a patient 10, such as a low battery or other error condition or warning. Still other components, provided as either part of the circuitry 80 of the ICM 12 or as external wirelessly-interfaceable devices, are possible.

In a further embodiment, the ECG front end circuit 83 of the ICM 12 measures raw dermal electrical signals using a driven reference signal, such as described in U.S. Pat. Nos. 9,700,227, 9,717,433, and 9,615,763, cited supra. The driven reference signal effectively reduces common mode noise, power supply noise and system noise, which is critical to preserving the characteristics of low amplitude cardiac action potentials, especially the P wave signals originating from the atria.

The ECG front end circuit 83 is organized into a passive input filter stage, a unity gain voltage follower stage, a passive high pass filtering stage, a voltage amplification and active filtering stage, and an anti-aliasing passive filter stage, plus a reference generator. The passive input filter stage passively shifts the frequency response poles downward to counter the high electrode impedance from the patient on the signal lead and reference lead, which reduces high frequency noise. The unity gain voltage follower stage allows the circuit to accommodate a very high input impedance, so as not to disrupt the subcutaneous potentials or the filtering effect of the previous stage. The passive high pass filtering stage includes a high pass filter that removes baseline wander and any offset generated from the previous stage. As necessary, the voltage amplification and active filtering stage amplifies or de-amplifies (or allows to pass-through) the voltage of the input signal, while applying a low pass filter. The anti-aliasing passive filter stage 75 provides an anti-aliasing low pass filter. The reference generator drives a driven reference signal containing power supply noise and system noise to the reference lead and is connected directly to the patient, thereby avoiding the thermal noise of the protection resistor that is included as part of the protection circuit 72.

Figure 13:
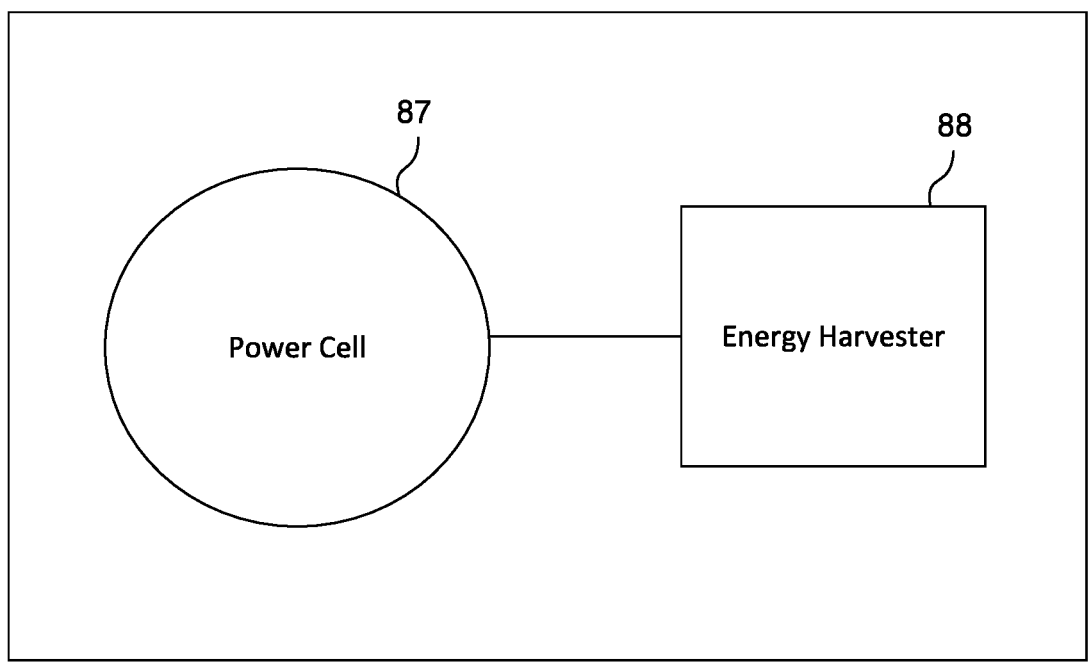
FIG. 13 is a diagram showing a power source of the ICM of FIG. 8 in accordance with one embodiment.

The ICM circuitry 80 further includes a power source 86 that is interfaced to other components of the circuitry 80 and powers those components. FIG. 13 is a diagram showing a power source 86 of the ICM 12 in accordance with one embodiment. The power source 86 includes a rechargeable power cell 87 and an energy harvesting module 88, which generates electrical energy based on input from an environment outside of the implantable housing, including when the implantable housing has been implanted within the patient 10. In one embodiment, the rechargeable power cell 87 can be a lithium-titanate battery, which recharges at a significantly faster rate due to an increased surface area at the anode (when compared to many other types of batteries). Other kinds of the rechargeable power cells 87 are also possible.

Figure 14:
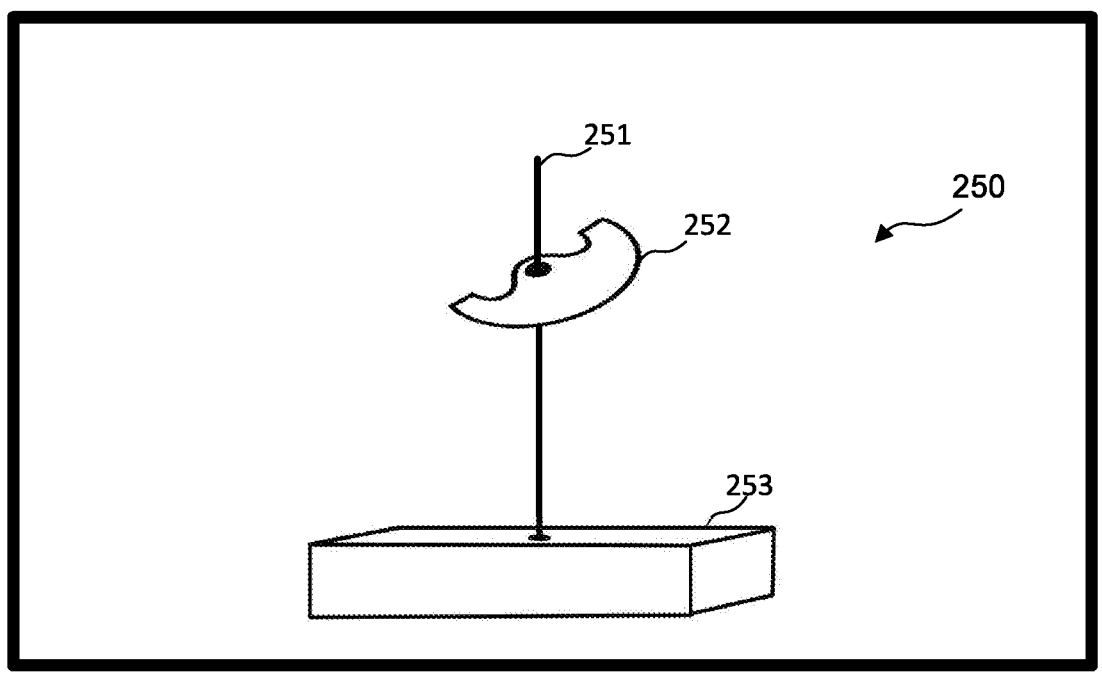
FIG. 14 is a diagram showing the energy harvesting module of FIG. 13 with a configuration to harvest kinetic energy in accordance with one embodiment.

While in the description below beginning with reference to FIG. 14 the energy harvesting module 88 is described as having a single energy-generating mechanism, in a further embodiment, a single energy harvesting module could combine multiple energy harvesting mechanisms (such as those described with reference to FIGS. 14-18). Further while particular embodiments of the energy harvesting module 88 are described with reference to FIGS. 14-18, other embodiments of the energy harvesting module 88 are also possible.

The energy harvesting module 88 can provide the harvested energy to the rechargeable power cell 87, recharging the power cell 87 and allowing the power cell 87 to power other components of the circuitry 80. In a further embodiment, the power cell 87 can be absent from the power source 86, and the electrical energy generated by the energy harvesting module 88 is the only electrical energy powering other components of the circuitry 87. Thus, the energy harvesting is either indirectly, via the power cell 87, or directly, interfaced to other components of the circuitry 80, providing power for those components of the circuitry 80.

Figure 9:
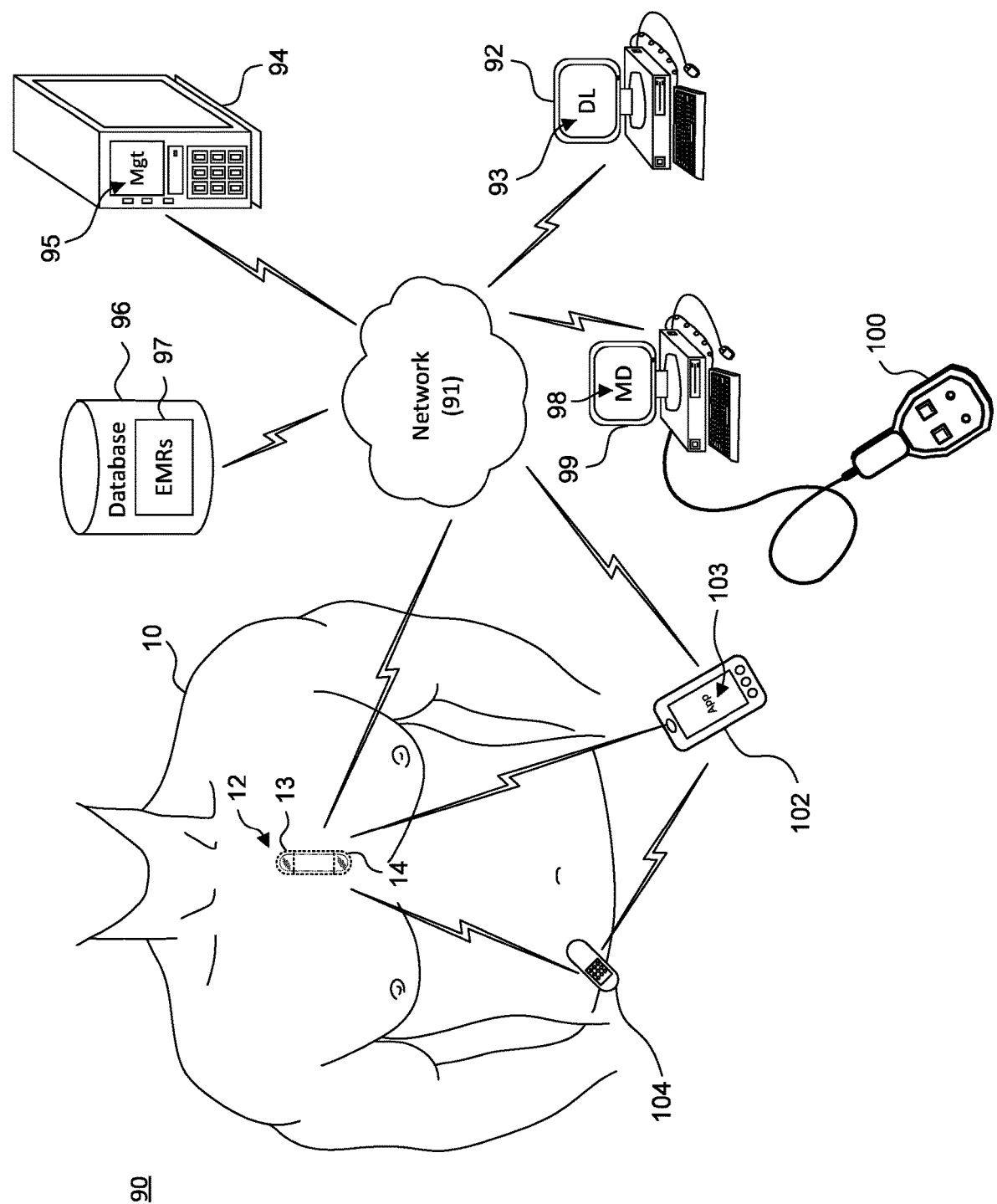
FIG. 9 is a functional block diagram showing a system for wirelessly interfacing with an ICM in accordance with one embodiment.

When operated standalone, the recording circuitry of the ICM 12 senses and records the patient's ECG data into an onboard memory. The ICM 12 can interoperate with other devices wirelessly through the transceiver 85. FIG. 9 is a functional block diagram showing a system 90 for wirelessly interfacing with an ICM 12 in accordance with one embodiment. The ICM 12 is designed for long-term electrocardiographic and physiological monitoring lasting up to several years in duration. During that time, stored data ECG monitoring data and other physiology and information will need to be offloaded and the ICM's firmware may need to be reprogrammed, and the transceiver 85 enables the ICM 12 to communicate with external devices to facilitate these functions.

In one embodiment, the ICM 12 can be wirelessly connected to a download station 92 executing data link software ("DL") 93 that permits the secure remote retrieval of stored ECG monitoring data, execution of diagnostics on or programming of the ICM 12, or performance of other functions. The ICM 12 connects to the download station 92 over a wireless network 91 via the transceiver 85. In turn, the download station 92 executes the data link software 93 or similar program that wirelessly interacts with the ICM 12 to retrieve the stored ECG monitoring data or perform other function. The download station 92 could be a server, personal computer, tablet or handheld computer, smart mobile device, or purpose-built programmer designed specific to the task of interfacing with a ICM 12, such as described below with reference to FIG. 19. Still other forms of download station 92 are possible.

Figure 12:
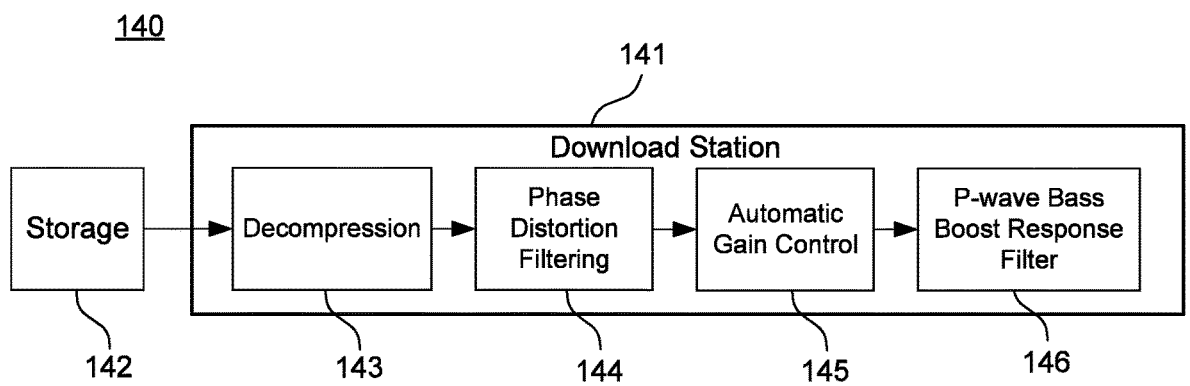
FIG. 12 is a functional block diagram showing the operations performed by the download station.

Upon retrieving stored ECG monitoring data from a ICM 12, middleware (not shown) executing on the download station 92 first operates on the retrieved data to adjust the ECG capture quality, as necessary, and to convert the retrieved data into a format suitable for use by third party post-monitoring analysis software, as further described infra with reference to FIG. 12. The formatted data can then be retrieved from the download station 92. The middleware could alternatively be executed by a separate device other than the download station 92.

A client-server model could be used to employ a server 94 to remotely interface with the download station 92 over the network 91 and retrieve the formatted data or other information. The server 94 executes a patient management program 95 ("Mgt") or similar application that stores the retrieved formatted data, recorded physiology, and other information in a secure database 96 cataloged in that patient's electronic medical records (EMRs) 97, along with tracking and correlating patient symptoms. In addition, the patient management program 95 could manage a subscription service that authorizes an ICM 12 to operate for a set period of time or under pre-defined operational parameters.

The patient management program 95, or other trusted application, also maintains and safeguards the secure database 96 to limit access to patient EMRs 97 to only authorized parties for appropriate medical or other uses, such as mandated by state or federal law, such as under the Health Insurance Portability and Accountability Act (HIPAA) or per the European Union's Data Protection Directive. For example, a physician may seek to review and evaluate his patient's ECG monitoring data, as securely stored in the secure database 96.

Physician and other authorized healthcare personnel are able to securely access the retrieved formatted data and other information stored in the EMRs 97 in the secure database 96 by executing an application program ("MD") 98, such as a post-monitoring ECG analysis program, on a personal computer 99 or other connectable computing device, and, through the application program 98, coordinate access to his patient's EMRs 97 with the patient management program 95 and perform other functions. The application program 98 can include the capability to actively or interactively diagnose or narrow down the underlying cause of sporadic cardiac conditions, for instance, atrial tachycardia (AT), AF, atrial flutter, AV node reciprocating tachycardia, ventricular tachycardia (VT), sinus bradycardia, asystole, complete heart block, and other cardiac arrhythmias. Other diagnoses are possible.

In a further embodiment, RR interval data can be extracted from the retrieved formatted data and be presented to physicians in a format that includes views of relevant near field and far field ECG data, which together provide contextual information that improves diagnostic accuracy, such as described in U.S. Pat. No. 9,408,551, issued Aug. 9, 2016 to Bardy et al., the disclosure of which is incorporated by reference. Both near field and far field ECG data views are temporally keyed to an extended duration RR interval data view. The durations of the classical "pinpoint" view, the pre- and post-event "intermediate" view, and the RR interval plot are flexible and adjustable. Thus, the pinpoint "snapshot" and intermediate views of ECG data with the extended term RR interval data allow a physician to comparatively view heart rate context and patterns of behavior prior to and after a clinically meaningful arrhythmia, patient concern or other indicia, thereby enhancing diagnostic specificity of cardiac rhythm disorders and providing physiological context to improve diagnostic ability. Similarly, the data wirelessly offloaded by the ICM can also be used to create a diagnostic composite plot of cardiac data, as further described in U.S.

Pat. No. 9,408,551, issued Aug. 9, 2016, the disclosure of which is incorporated by reference. As the amount of data necessary to construct an RR interval plot can be as large as 0.25 megabyte, the energy provided by the energy harvesting module 88 becomes critical for continuous offloading of the collected data at rates high enough to enable such processing.

As a result, with the assistance of the server 94, a complete end-to-end closed loop of patient care can be provided, with the ICM 12 providing long-term ECG and physiology monitoring and data reporting, the patient management program 95 managing ECG and physiology data retrieval and patient symptom tracking and correlation, the application program 98 empowering physicians with the ability to effectively identify the underlying cause of sporadic cardiac conditions, particularly cardiac rhythm disorders, and the ICM 12 again facilitating patient following upon diagnosis and throughout treatment.

In a further embodiment, the ICM 12 can interoperate wirelessly with other physiology monitors and activity sensors 104, whether implanted or dermal, such as activity trackers worn on the wrist or body, and with mobile devices 102, including smartphones and smart watches, that are designed to communicate over a public communications infrastructure, such as a cellular communications network. Wearable physiology monitors and activity sensors 104 encompass a wide range of wirelessly interconnectable devices that measure or monitor a patient's physiological data, such as heart rate, temperature, blood pressure, respiratory rate, blood pressure, blood sugar (with appropriate subcutaneous probe), oxygen saturation, minute ventilation, and so on; physical states, such as movement, sleep, footsteps, and the like; and performance, including calories burned or estimated blood glucose level.

The physiology sensors in non-wearable mobile devices 102, particularly smartphones, are generally not meant for continuous tracking and do not provide medically precise and actionable data sufficient for a physician to prescribe a surgical, catheter or serious drug intervention; such data can be considered screening information that something may be wrong, but not data that provides the highly precise information that may allow for a surgery, such as implantation of a pacemaker for heart block or a defibrillator for ventricular tachycardia, or the application of serious medications, like blood thinners for atrial fibrillation or a cardiac ablation procedure. Such devices, like smartphones, are better suited to pre- and post-exercise monitoring or as devices that can provide a signal that something is wrong, but not in the sufficient detail and FDA approved, legally meaningful validation to allow for medical action. Conversely, medically actionable wearable sensors and devices sometimes provide continuous recording for relatively short time periods, up to 80 days, but do not span years and, further, must be paired with a smartphone or computer to offload and evaluate the recorded data, especially if the data is of urgent concern.

Wearable physiology monitors and activity sensors 104, also known as "activity monitors," and to a lesser extent, "fitness" sensor-equipped mobile devices 102, can trace their life-tracking origins to ambulatory devices used within the medical community to sense and record traditional medical physiology that could be useful to a physician in arriving at a patient diagnosis or clinical trajectory, as well as from outside the medical community, from, for instance, sports or lifestyle product companies who seek to educate and assist individuals with self-quantifying interests. Data is typically tracked by the wearable physiology monitors or activity sensors 104 and mobile device 102 for only the personal use of the wearer. The physiological monitoring is strictly informational, even where a device originated within the medical community, and the data is generally not time-correlated to physician-supervised monitoring. Importantly, medically-significant events, such as cardiac rhythm disorders, including tachyarrhythmias, like ventricular tachycardia or atrial fibrillation, and bradyarrhythmias, like heart block, while potentially detectable with the appropriate diagnostic heuristics, are neither identified nor acted upon by the wearable physiology monitors and activity sensors 104 and the mobile device 102.

Frequently, wearable physiology monitors and activity sensors 104 are capable of wirelessly interfacing with mobile devices 102, particularly smart mobile devices, including so-called "smartphones" and "smart watches," as well as with personal computers and tablet or handheld computers, to download monitoring data either in real-time or in batches. The wireless interfacing of such activity monitors is generally achieved using transceivers that provide low-power, short-range wireless communications, such as Bluetooth, although some wearable physiology monitors and activity sensors 104, like their mobile device cohorts, have transceivers that provide true wireless communications services, including 4G or better mobile telecommunications, over a telecommunications network. Other types of wireless and wired interfacing are possible.

In a further embodiment, where the wearable physiology monitors and activity sensors 104 are paired with a mobile device 102, the mobile device 102 executes an application ("App") 103 that can retrieve the data collected by the wearable physiology monitor and activity sensor 104 and evaluate the data to generate information of interest to the wearer, such as an estimation of the effectiveness of the wearer's exercise efforts. Where the wearable physiology monitors and activity sensors 104 has sufficient onboard computational resources, the activity monitor itself executes an app without the need to relay data to a mobile device 102. The app can include or be supplemented by downloadable programming instructions, including machine learning and other forms of artificial intelligence-originated instructions. The app can include heuristics to signal patient and physician with alerts over health conditions or arrhythmias of selected medical concern, such as where a heart pattern particular to the patient is identified and the mobile device 102, in collaboration with the ICM 12, is thereby reprogrammed to watch for a reoccurrence of that pattern, after which an alert will be generated and sent to the physician (or other caregiver). Similarly, the app can include heuristics that can actively identify or narrow down a pattern (or even the underlying cause) of sporadic cardiac conditions, for instance, atrial tachycardia (AT), atrial fibrillation (AF), atrial flutter (AFL), AV node reciprocating tachycardia, ventricular tachycardia (VT), sinus bradycardia, asystole, complete heart block, and other cardiac arrhythmias, again, after which an alert will be generated and sent to the physician (or other caregiver). For instance, an alert that includes a compressed ECG digitized sample can also be wirelessly transmitted by the app upon the triggering of a preset condition, such as an abnormally low heart rate in excess of 170 beats per minute (bpm), an abnormally low heart rate falling below 30 bpm, or AF detected by onboard analysis of RR interval variability by the app. Finally, a similar methodology of creating app programming tailored to the monitoring and medical diagnostic needs of a specific patient (or patient group or general population) can be used for other conditions or symptoms, such as syncope, palpitations, dizziness and giddiness, unspecified convulsions, abnormal ECG, transient cerebral ischemic attacks and related syndromes, cerebral infarction, occlusion and stenosis of pre-cerebral and cerebral arteries not resulting in cerebral infarction personal history of transient ischemic attack, and cerebral infarction without residual deficits, to trigger an alert and involve the physician or initiate automated analysis and follow up back at the patient's clinic. Still other activity monitor and mobile device functions on the collected data are possible.

In a yet further embodiment, a wearable physiology monitor, activity sensor 104, or mobile device 102 worn or held by the patient 10, or otherwise be used proximal to the patient's body, can be used to first obtain and then work collaboratively with the more definitive and capable ICM 12 to enable the collection of physiology by the ICM 12 before, during, and after potentially medically-significant events. The wearable physiology monitor, activity sensor 104, or mobile device 102 must be capable of sensing cardiac activity, particularly heart rate or rhythm, or other types of physiology or measures, either directly or upon review of relayed data. Where the wearable physiology monitor or activity sensor 104 is paired with a mobile device 102, the mobile device 102 serves as a relay device to trigger a medical alert upon detecting potentially medically-significant events in the data provided by the paired activity monitor, such as cardiac rhythm disorders, including tachyarrhythmias and bradyarrhythmias. Finally, if the wearable physiology monitor or activity sensor 104 has sufficient onboard computational resources and also is equipped with a wireless communications services transceiver, the wearable physiology monitor or activity sensor 104 effectively becomes the mobile device and executes an application (not shown) that will trigger the medical alert directly. Still other configurations of the detection app are possible.

In a still further embodiment, the monitoring data recorded by the ICM 12 can be uploaded directly into the patient's EMRs 97, either by using a mobile device 102 as a conduit for communications with the secure database 96 via the server 94, or directly to the server 94, if the ICM 12 is appropriately equipped with a wireless transceiver 85 (shown with reference to FIG. 8) or similar external data communications interface. As described below, the wireless data offloaded from the ICM 12 can be used in a variety of ways, with the use requiring a frequent wireless transmission of large collected data sets, including full disclosure HRV. Such frequent transmission of large data sets is made possible by the presence of the energy harvesting module 88 described below. Further, the availability of the energy harvesting module 88 allows to increase the amount of power used by the wireless transceiver 85 to allow fast and efficient data transfer rates through subcutaneous fat of the patient 10. The increased amount of power used by the wireless transceiver 85 can be pre-set prior to the implantation of the ICM 12, or done following the implantation. For example, the amount of power used by the wireless transceiver 85 can be wirelessly adjusted by an external programmer (such as upon the rates of data transfer from the ICM 12 being unsatisfactory), or done by the microcontroller 81 upon detection that the rates of data transfer are below a threshold level.

Thus, the data recorded by the ICM 12 would directly feed into the patient's EMRs 97, thereby allowing the data to be made certifiable for immediate use by a physician or authorized healthcare provider. No intermediate steps would be necessary when going from subcutaneously sensing cardiac electric signals and collecting the patient's physiology using a ICM 12 to presenting that recorded data to a physician or healthcare provider for medical diagnosis and care. The direct feeding of data from the ICM 12 to the EMRs 97 clearly establishes the relationship of the data, as recorded by the ICM 12, to the patient 10 that the physician is seeing and appropriately identifies any potentially medically-significant event recorded in the data as originating in the patient 10 and nobody else. Based on the monitoring data, physicians and healthcare providers can rely on the data as certifiable and can directly proceed with determining the appropriate course of treatment for the patient 10, including undertaking further medical interventions as appropriate.

In a yet further embodiment, the server 94 can evaluate the recorded data, as fed into the patient's EMRs 97, to refer the patient 10 for medical care to a general practice physician or medical specialist, for instance, a cardiac electrophysiologist referral from a cardiologist when the recorded data indicates an event of sufficient potential severity to warrant the possible implantation of a pacemaker for heart block or a defibrillator for ventricular tachycardia. Other uses of the data recorded by the ICM 12 are possible. For instance, a patient 10 who has previously suffered heart failure is particularly susceptible to ventricular tachycardia following a period of exercise or strenuous physical activity. A wearable sensor 104 or device 102 that includes a heart rate monitor would be able to timely detect an irregularity in heart rhythm. The application executed by the sensor 104 or device 102 allows those devices to take action by triggering the dispatch of a ICM 12 to the patient 10, even though the data recorded by the sensor 104 or device 102 is itself generally medically-insufficient for purposes of diagnosis and care. Thus, rather than passively recording patient data, the sensor 104 or device 102 takes on an active role in initiating the provisioning of medical care to the patient 10 and starts a cascade of appropriate medical interventions under the tutelage of and followed by physicians and trained healthcare professionals.

In a still further embodiment, based upon machine learning instructions executed by the ICM 12 that generates alerts over health conditions or arrhythmias of selected medical concern, the ICM 12 could upload an event detection application to the sensor 104 or device 102 to enable those devices to detect those types of potentially medically-significant events. Alternatively, the event detection application could be downloaded to the sensor 104 or device 102 from an online application store or similar online application repository. Finally, the ICM 12 could use the sensor 104 or device 102 to generate an appropriate alert, including contacting the patient's physician or healthcare services, via wireless (or wired) communications, upon detecting a potentially medically-significant event or in response to a patient prompting.

The mobile device 102 could also serve as a conduit for providing the data collected by the wearable physiology monitor or activity sensor 104 to a server 122, or, similarly, the wearable physiology monitor or activity sensor 104 could itself directly provide the collected data to the server 122. The server 122 could then merge the collected data into the wearer's EMRs 134 in the secure database 124, if appropriate (and permissible), or the server 122 could perform an analysis of the collected data, perhaps based by comparison to a population of like wearers of the wearable physiology monitor or activity sensor 104. Still other server 122 functions on the collected data are possible.

Finally, in a yet further embodiment, the ICM 12 can be interrogated using a conventional inductive programmer 100, which could be interfaced to the application program 98 executing on a physician's device, or in a standalone fashion. Inductive interfacing may be necessary where the transceiver 85 has suffered an error condition or is otherwise unable to communicate externally.

Figure 10:
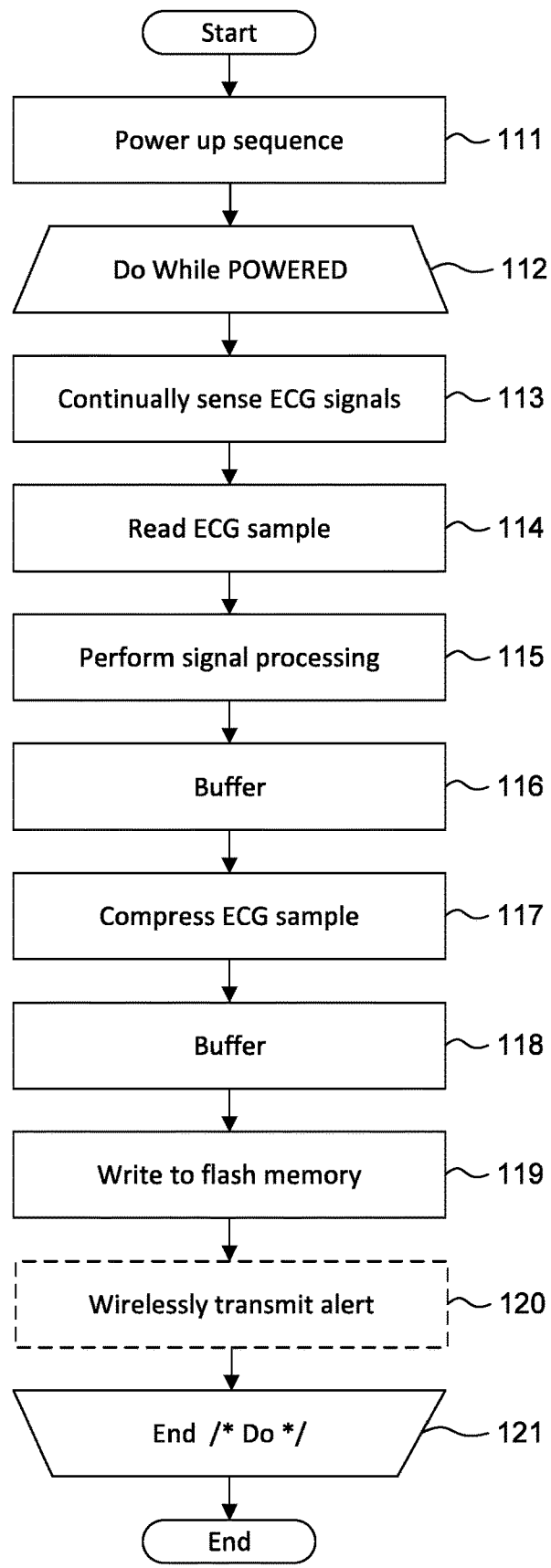
FIG. 10 is a flow diagram showing an ICM-implemented method for monitoring ECG data.

The ICM 12 continuously monitors the patient's ECG, heart rate and physiology over a long period of time lasting up to several years in duration. FIG. 10 is a flow diagram showing an ICM-implemented method 110 for monitoring ECG data. Initially, upon successful implantation, the microcontroller 61 executes a power up sequence (step 111). During the power up sequence, the voltage of the battery is checked, the state of the flash memory 62 is confirmed, both in terms of operability check and available capacity, and microcontroller operation is diagnostically confirmed.

Following satisfactory completion of the power up sequence, an iterative processing loop (steps 112-121) is continually executed by the microcontroller 61. During each iteration (step 112) of the processing loop, the ECG frontend 63 (shown in FIG. 11) continually senses the dermal ECG electrical signals (step 113, FIG. 10) via the ECG electrodes 16 and 17 and is optimized to maintain the integrity of the P-wave. A sample of the ECG signal is read (step 114) by the microcontroller 61 by sampling the analog ECG signal that is output by the ECG front end circuit 63. Each sampled ECG signal, in quantized and digitized form, is processed by signal processing modules as specified in firmware (step 115), as described infra, and temporarily staged in a buffer (step 116), pending compression preparatory to storage in the flash memory 62 (step 117). Following compression, the compressed ECG digitized sample is again buffered (step 118), then written to the flash memory 62 (step 119) using the communications bus. In a further embodiment, an alert that includes the compressed ECG digitized sample can also be wirelessly transmitted upon the triggering of a preset condition (step 120), such as an abnormally low heart rate in excess of 170 beats per minute (bpm), an abnormally low heart rate falling below 30 bpm, or AF detected by onboard analysis of RR interval variability by the microcontroller 61. Processing continues for an indefinite duration (step 121). Still other operations and steps are possible.

The microcontroller 61 operates under modular micro program control that includes processing of raw analog ECG signals. FIG. 11 is a functional block diagram showing the signal processing functionality 130 of the microcontroller 61. The microcontroller 61 operates under modular micro program control as specified in firmware 132. The firmware modules 132 include high and low pass filtering 133, and compression 134. Other modules are possible. The microcontroller 61 has a built-in ADC, although ADC functionality could also be provided in the firmware 132.

The ECG front end circuit 63 first outputs an analog ECG signal, which the ADC 131 acquires, samples and converts into an uncompressed digital representation. The microcontroller 61 includes one or more firmware modules 133 that perform filtering. In one embodiment, three low pass filters and two high pass filters are used. Following filtering, the digital representation of the cardiac activation wave front amplitudes are compressed by a compression module 134 before being written out to storage 135.

The download station 92 (shown in FIG. 9) executes a data link program ("DL") 93 or similar program that wirelessly interfaces with the ILR 12 to retrieve the stored ECG monitoring data and perform other functions. FIG. 12 is a functional block diagram showing the operations 140 performed by the download station 141. The download station 141 could be a server, personal computer (as shown), tablet or handheld computer, smart mobile device, or purpose-built programmer designed specific to the task of wirelessly interfacing with a ICM 12. Still other forms of download station are possible, including download stations connected through indirect wireless interfacing using, for instance, a smart phone connected to the ICM 12 through Bluetooth or Wi-Fi, or over an inductive coupling.

The download station 141 is responsible for offloading stored ECG monitoring data from a ICM 12. The download station 141 operates under programmable control as specified in software. The stored ECG monitoring data remotely retrieved from storage 142 on a ICM 12 is first decompressed by a decompression module 143, which converts the stored ECG monitoring data back into an uncompressed digital representation more suited to signal processing than a compressed signal. The retrieved ECG monitoring data may be stored into local storage (not shown) for archival purposes, either in original compressed form, or as uncompressed.

The download station 141 can include an array of filtering modules. For instance, a set of phase distortion filtering tools 144 may be provided, where corresponding software filters can be provided for each filter implemented in the firmware executed by the microcontroller 61. The digital signals are run through the software filters in a reverse direction to remove phase distortion. For instance, a 45 Hertz high pass filter in firmware may have a matching reverse 45 Hertz high pass filter in software. Most of the phase distortion is corrected, that is, canceled to eliminate noise at the set frequency, but data at other frequencies in the waveform remain unaltered. As well, bidirectional impulse infinite response (IIR) high pass filters and reverse direction (symmetric) IIR low pass filters can be provided. Data is run through these filters first in a forward direction, then in a reverse direction, which generates a square of the response and cancels out any phase distortion. This type of signal processing is particularly helpful with improving the display of the ST-segment by removing low frequency noise.

An automatic gain control (AGC) module 145 can also be provided to adjust the digital signals to a usable level based on peak or average signal level or other metric. AGC is particularly critical to single-lead ECG monitors, where physical factors, such as the tilt of the heart, can affect the electrical field generated. On three-lead Holter monitors, the leads are oriented in vertical, horizontal and diagonal directions. As a result, the horizontal and diagonal leads may be higher amplitude and ECG interpretation will be based on one or both of the higher amplitude leads. In contrast, the ICM 12 has only a single lead that is oriented in the vertical direction, so variations in amplitude will be wider than available with multi-lead monitors, which have alternate leads to fall back upon.

In addition, AGC may be necessary to maintain compatibility with existing ECG interpretation software, which is typically calibrated for multi-lead ECG monitors for viewing signals over a narrow range of amplitudes. Through the AGC module 145, the gain of signals recorded by the ICM 12 of the electrocardiography monitor 12 can be attenuated up (or down) to work with FDA-approved commercially available ECG interpretation.

AGC can be implemented in a fixed fashion that is uniformly applied to all signals in an ECG recording, adjusted as appropriate on a recording-by-recording basis. Typically, a fixed AGC value is calculated based on how an ECG recording is received to preserve the amplitude relationship between the signals. Alternatively, AGC can be varied dynamically throughout an ECG recording, where signals in different segments of an ECG recording are amplified up (or down) by differing amounts of gain.

Typically, the ICM 12 will record a high resolution, low frequency signal for the P-wave segment similar to the ICM's dermal cousin, such as provided with the dermal ambulatory monitors cited supra. However, for some patients, the result may still be a visually small signal. Although high resolution is present, the unaided eye will normally be unable to discern the P-wave segment. Therefore, gaining the signal is critical to visually depicting P-wave detail. This technique works most efficaciously with a raw signal with low noise and high resolution, as typically generated by the ICM 12. Automatic gain control applied to a high noise signal will only exacerbate noise content and be self-defeating.

Finally, the download station can include filtering modules specifically intended to enhance P-wave content. For instance, a P-wave based boost filter 146, which is a form of a pre-emphasis filter, can be applied to the signal to restore missing frequency content or to correct phase distortion. Still other filters and types of signal processing are possible.

In one embodiment, the ICM 12 can simply be inserted with a small surgical incision that is the width of the widest part of the ICM, typically the transverse cross section of the thickest aspect of the housing 15. Blunt dissection thereafter under local anesthesia can be used to create the subcutaneous space to receive the ICM 12, which would generally be inserted into the implantation site, proximal (housing) end first, followed by the distal (electrode assembly) end. In a further embodiment, the ICM 12 can be implanted in the patient's chest using, for instance, a minimally invasive subcutaneous implantation instrument, such as described in U.S. Pat. No. 6,436,068, issued Aug. 20, 2002 to Bardy, the disclosure of which is incorporated by reference.

The energy harvesting module 88 provides a way to continually obtain additional energy for powering the ICM 12 while implanted within the patient 10, potentially extending the term of use of the ICM 12 to the lifetime of the patient. One source of the energy being harvested can be the kinetic energy generated by the patient 10. FIG. 14 is a diagram showing the energy harvesting module 88 of FIG. 13 with a configuration to harvest kinetic energy in accordance with one embodiment. In this embodiment, the energy harvesting module 88 includes an electrical motor 250 that is composed of a rotor 251 that is integrated into a stator 253, with the stator 253 producing electrical energy upon the rotation of the rotor 251. An oscillating weight 252 is fixedly attached to the rotor 251. The weight 252 pivots during normal movements of the patient due to the changes in the position of the patient's body (such as getting up, lying or sitting down, walking, and exercising). The pivoting of the weight 252 causes the rotation of the rotor 251, which causes the stator 253 to produce electrical energy. While the weight is shown to be of a particular shape with reference to FIG. 14, other shapes of the weight 253 are also possible. The generated electrical energy is provided either to the power cell 87 or directly to other components of the circuitry 80 of the ICM 12. In one embodiment, the production of electrical energy by the energy harvesting module can be detected by the microcontroller 81 and recorded into the flash memory 82 as an indication of the patient moving during the time the energy harvesting module 88 produces the energy. Such movement data can subsequently be unloaded and processed along with the electrophysiological data collected by the ICM 12 and provide additional context for any cardiac events.

Figure 15:
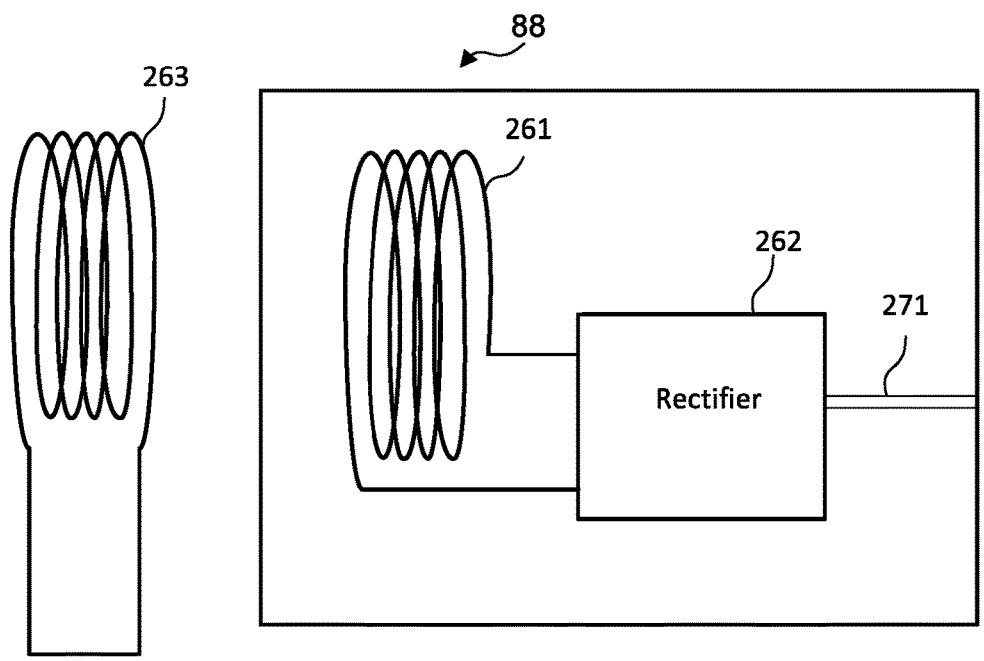
FIG. 15 is a diagram showing the energy harvesting module of FIG. 13 with a configuration to receive energy from an external inductive coil via inductive coupling in accordance with one embodiment.

The energy harvesting module 88 can also harvest energy that is deliberately directed at the ICM 12. FIG. 15 is a diagram showing the energy harvesting module 88 of FIG. 13 with a configuration to receive energy from an external inductive coil via inductive coupling in accordance with one embodiment. In this embodiment, the energy harvesting module 88 includes an inductive coil 261 that generates alternating current upon being exposed to a magnetic field generated by a further coil 263 located outside the patient 10. Thus, when the ICM 12 is implanted into the patient 10, the external coil 263 (which can be included in a wand operated by qualified medical personnel) can be positioned in proximity to the patient's chest, with the external coil 263 generating a magnetic field upon electricity being ran through the external coil 263. The magnetic field induces the generation of the alternating current within the inductive coil 261 within the energy harvesting module 88 in accordance with Faraday's law of induction. The generated alternated current is provided to a rectifier 262, which converts the alternating current to direct current is provided either to the power cell 87 or directly to other components of the circuitry 80 of the ICM (such as via wires 271). The transfer of energy to the inductive coil 261 can be performed at the same time as offloading of data collected by the ICM 12, as further described below with reference to FIG. 19.

Figure 16:
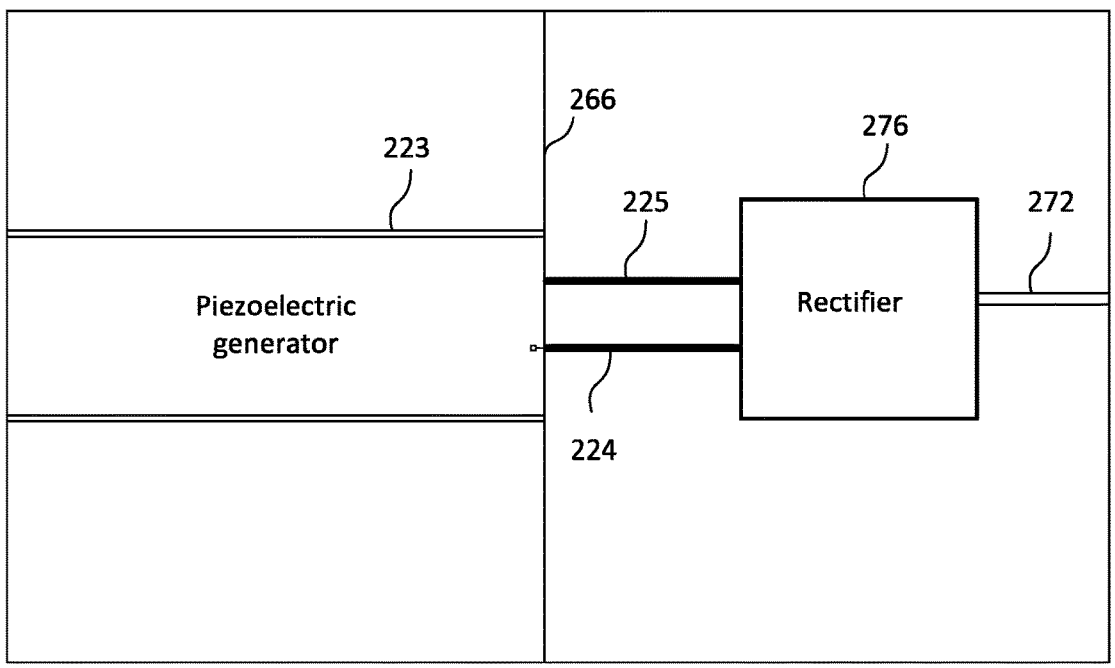
FIG. 16 is a diagram showing the energy harvesting module of FIG. 13 with a configuration that includes a piezoelectric energy generator in accordance with one embodiment.

Vibrations that the ICM 12 is exposed while being inside the patient's body, which can be caused either by the patient's movements or caused by external factors, can also be harvested and used for energy generation. FIG. 16 is a diagram showing the energy harvesting module 88 of FIG. 13 with a configuration that includes a piezoelectric energy generator 223 in accordance with one embodiment. The generator 223 includes a piece of piezoelectric material, such as piezoelectric rubber, that is stretched (under tension) on a partition 267 within the energy harvesting module 88. Upon vibrations reaching the energy harvesting module 88, the vibrations cause a deformation of the stretched piezoelectric material, which produces alternating current. The piezoelectric generator 88 is interfaced via wires 224, 225 to a rectifier 226, which converts the alternating current to direct current, which in turn is provided either to the power cell 87 or directly to other components of the circuitry 80 of the ICM 12 (such as via wires 172). In one embodiment, the vibrations that the energy harvesting module 88 harvests to produce electrical energy can be vibrations of caused by the patient's heartbeat, though other sources of vibrations are possible.

Figure 17:
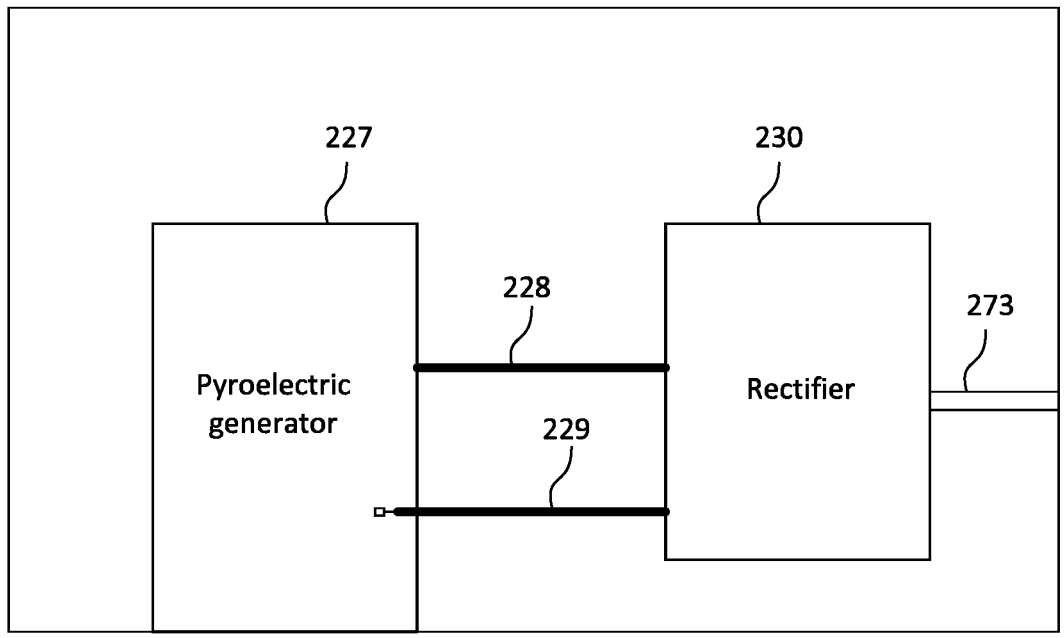
FIG. 17 is a diagram showing the energy harvesting module of FIG. 13 with a configuration to generate electrical energy upon a change in the patient's bodily temperature in accordance with one embodiment.

The patient's bodily temperature fluctuates depending on time of day, activity level, dietary intake, and other factors. This fluctuation in temperature can be taken advantage of to generate electrical energy for the ICM 12. FIG. 17 is a diagram showing the energy harvesting module 88 of FIG. 13 with a configuration to generate electrical energy upon a change in the patient's bodily temperature in accordance with one embodiment. In this embodiment, the energy harvesting module 88 includes a pyroelectric material 227, such as a pyroelectric crystal (though other pyroelectric materials are also possible) that generates alternating current upon the change in the temperature of the patient's body (and consequently, the change in the temperature of the pyroelectric material). The pyroelectric material 227 is interfaced via wires 228, 229 to a rectifier 240, which converts the alternating current to direct current, which in turn is provided either to the power cell 87 or directly to other components of the circuitry 80 of the ICM 12 (such as via wires 173).

Figure 18:
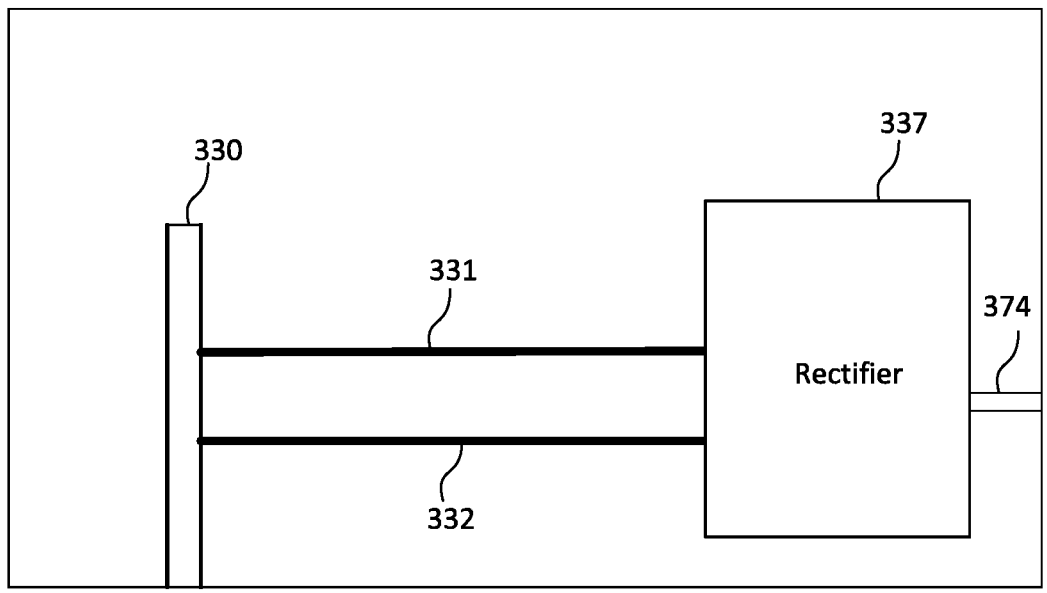
FIG. 18 is a diagram showing the energy harvesting module of FIG. 13 with a configuration to harvest energy of radio waves in accordance with one embodiment.

A further source of energy that the energy harvesting module 88 can take advantage of are radio waves, which are plentiful in most populated areas. FIG. 18 is a diagram showing the energy harvesting module 88 of FIG. 13 with a configuration to harvest energy of radio waves in accordance with one embodiment. In this embodiment, at least a portion (such as one side) of the housing 15 of the ICM 12 is made of a material that is transparent to radio waves, such as plastic, though other radio transparent materials are possible. The energy harvesting module 88 includes an antenna 330 that generates alternating current upon capturing radio waves originating from outside the patient's body. The antenna 330 is interfaced by wires 331, 332 to a rectifier 337, such as a diode (though other rectifiers are possible) that converts the alternating current to direct current, and which supplies the direct current either to the power cell 87 or directly to other components of the circuitry 80 of the ICM 12 (such as via wires 374). In one embodiment, the antenna 330 could be a folded unipole antenna. In a further embodiment, the antenna 330 could be a dipole antenna. Still other kinds of antennas 330 are possible. While the antenna 330 is shown to be compartmentalized to the energy harvesting module 88 of the ICM 12, in a further embodiment, at least a portion of the antenna 330 can be located in other portions of the housing 15, such as being wrapped around the internal periphery of the housing 15. In a still further embodiment, at least a portion of the antenna 330 could be located on the outside of the housing 15. Further, while the antenna 330 could be a stand-alone antenna that only has the function of harvesting power (with a different antenna being used by the wireless transceiver 85 for communication and data offloading), in a further embodiment, the antenna 330 could also be used by the wireless transceiver 85 to offload collected data and other wireless communication, with no additional antenna used exclusively by the wireless transceiver 85 being included in the ICM 12.

Figure 19:
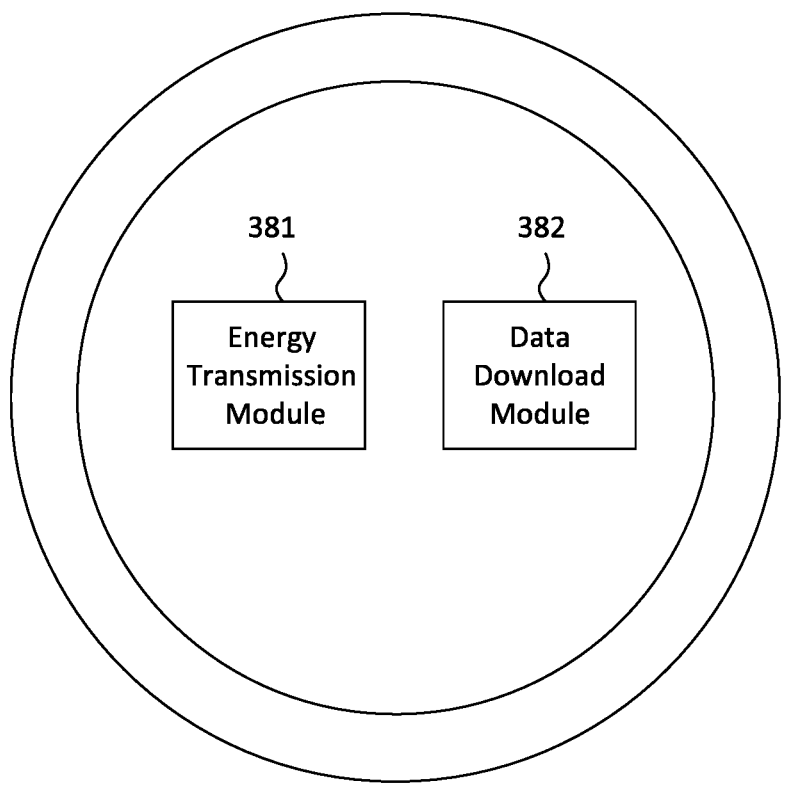
FIG. 19 is a diagram showing an external device combining energy transmission and data download capabilities for use with the ICM in accordance with one embodiment.

While the energy harvesting module 88 can produce electrical energy using radio waves originating from many sources outside of the patient's body, the radio waves can also be specifically directed at the energy harvesting module. Thus, a properly-trained patient or a qualified medical professional can use an external source of the radio waves to specifically provide the power to the energy harvesting module 88. The source of radio waves can also include the capability to wirelessly receive data collected by the ICM 12, which the ICM 12 can offload at the same time as the energy harvesting module 88 is receiving energy. FIG. 19 is a diagram showing an external device 380 combining energy transmission and data download capabilities for use with the ICM 12 in accordance with one embodiment. The external device 380 can be shaped as a puck that can be pressed against (or held close to) the patient's chest in the parasternal region at the level at which the ICM 12 is implanted. The external device 380 includes an energy transmission module 381 that is capable of interfacing with the energy harvesting module 88 to provide input (such as magnetic or radio waves) that allows the energy harvesting module 88 to produce electrical energy. For example, the energy transmission module 381 can include a radio transmitter that radiates radio waves captured by the antenna 330. The energy transmission can also include, alternatively or in addition to the radio transmitter, the further inductive coil 263 that generates the magnetic field that causes the inductive coil 261 within the energy harvesting module 283.

Further, the external device 380 includes a data download module 382, which uses an internal wireless transceiver to wirelessly download data collected by the ICM 12 by interfacing with the wireless transceiver 85 of the ICM 12. The downloading of the data can happen simultaneously to the energy transmission module 381 supplying the input to the energy harvesting module 88 of the ICM, allowing to reduce the time that the external device 380 would need to be held next to the patient 10. The downloaded physiological data can in turn wirelessly forwarded by the external device 380 for further processing, such as to the server 94. The external device 380 can also perform processing of the downloaded data, as described above with reference to FIG. 12, prior to transmitting the data to the server 14. The external device 380 further includes components necessary for the functioning of the modules 381 and 382 and other processing, such as a processor, memory, and either an internal source of power, or a connection to an external source of power.

In addition, while the external device is shown as a puck with reference to FIG. 19, in a further embodiment, other configurations of the external device 380 are possible. For example, the external device 380 could be shaped as a wand. Still other configurations of the external device are possible.

While the invention has been particularly shown and described as referenced to the embodiments thereof, those skilled in the art will understand that the foregoing and other changes in form and detail may be made therein without departing from the spirit and scope.

What is claimed is:

1. An insertable cardiac monitor with internal energy harvesting capabilities, comprising:
    an implantable housing comprised of a biocompatible material that is suitable for implantation within a living body;
    at least one pair of ECG sensing electrodes provided with the implantable housing operatively placed to facilitate monitoring of cardiac action potentials from the subcutaneous thoracic space that are generated during atrial activation;
    electronic circuitry provided within the housing assembly comprising a low power microcontroller, an ECG front end circuit interfaced to the microcontroller and configured to capture the cardiac action potentials sensed by the pair of ECG sensing electrodes which are output as ECG signals, and a memory electrically interfaced with the microcontroller and operable to store data from the ECG signals sensed with substantially every heartbeat; and
    an energy harvesting module electrically interfaced to the electronic circuitry and configured to generate electrical energy based on input from an environment outside of the implantable housing when the implantable housing is implanted into the living body, wherein at least a portion of generated electrical energy is used by the electronic circuitry, the energy harvesting module further comprising:
        a rotor a portion of which is engaged to a stator;
        a weight attached to a further portion of the rotor, wherein movements of the living body causes a rotation of the weight when the implantable housing is within the living body, the rotation of the pivoted body causing a rotation of the rotor; and
        the stator configured to generate the electrical energy upon the rotation of the portion of the rotor engaged to the stator.

2. A subcutaneous insertable cardiac monitor in accordance with claim 1, the energy harvesting module further comprising:

an inductive coil configured to generate alternating current upon being exposed to a magnetic field generated by a further coil located outside the living body; and a rectifier interfaced to the inductive coil and configured to convert the alternating current to direct current, wherein the direct current is provided to the electrical circuitry as the electrical energy.

3. A subcutaneous insertable cardiac monitor in accordance with claim 1, the energy harvesting module further comprising:

a piezoelectric material configured to generate alternating current upon the implantable housing receiving kinetic energy when the implantable housing is inside the living body;

a rectifier interfaced to the piezoelectric material and configured to convert the alternating current to direct current, wherein the direct current is provided to the electrical circuitry as the electrical energy.

4. A subcutaneous insertable cardiac monitor in accordance with claim 3, wherein the piezoelectric material comprises piezoelectric rubber and the kinetic energy comprises is delivered via vibrations of implantable housing.

5. A subcutaneous insertable cardiac monitor in accordance with claim 1, the energy harvesting module further comprising:

a pyroelectric crystal configured to generate alternating current upon a change in a temperature of the living body when the implantable housing is implanted within the living body; and a rectifier interfaced to the pyroelectric crystal and configured to convert the alternating current to direct current, wherein the direct current is provided to the electrical circuitry as the electrical energy.

6. A subcutaneous insertable cardiac monitor in accordance with claim 1, the energy harvesting module further comprising:

an antenna within the implantable housing configured to generate alternating current upon receiving radio waves from outside the housing when the implantable housing is implanted within the living body; and a diode interfaced to the antenna and configured to convert the alternating current to direct current, wherein the direct current is provided to the electrical circuitry as the electrical energy.

7. A subcutaneous insertable cardiac monitor in accordance with claim 6, wherein at least a portion of the implantable housing is composed of a radio transparent material.

8. A subcutaneous insertable cardiac monitor in accordance with claim 7, wherein the radio transparent material is plastic.

9. A subcutaneous insertable cardiac monitor in accordance with claim 1, further comprising:

a rechargeable power cell interfaced to the electronic circuitry and configured to power the electronic circuitry, wherein the energy harvesting module supplies the electrical energy to the power cell.

10. A subcutaneous insertable cardiac monitor in accordance with claim 9, wherein the rechargeable power cell is a lithium-titanate battery.

11. A subcutaneous insertable cardiac monitor in accordance with claim 1, wherein the energy harvesting module is a sole electrical energy source for the electronic circuitry.

12. A subcutaneous insertable cardiac monitor in accordance with claim 1, further comprising:

at least one further ECG sensing electrode further provided to wraparound an end of the implantable housing circumferentially about one of the pair of ECG sensing electrodes, continue around the sides and ends of the implantable housing, and over the planar surface of the implantable housing, wherein the firmware comprises programmatic selection of one or more pairings of the ECG sensing electrodes.

13. A subcutaneous insertable cardiac monitor in accordance with claim 12, further comprising:

a periphery interposed between the at least one further ECG sensing electrode and the at least one further ECG sensing electrode, wherein the firmware comprises programmatic control over the electrically insulative properties of the periphery relative to the at least one further ECG sensing electrode and the at least one further ECG sensing electrode.

14. A subcutaneous insertable cardiac monitor in accordance with claim 1, the electronic circuitry further comprising:

a transceiver operable to wirelessly interface to an external device through which to at least one of provide the samples of the ECG signals from the non-volatile memory and receive modular micro program control into the firmware.

15. A subcutaneous insertable cardiac monitor in accordance with claim 14, wherein the transceiver provides the samples of the ECG signals at the same time as the energy harvesting module generates the electrical energy based on the input from the external device.

16. A subcutaneous insertable cardiac monitor in accordance with claim 15, wherein the firmware comprises instructions operable to program the microcontroller to perform the steps comprising:

monitoring the cardiac action potentials sensed by the pair of ECG sensing electrodes for arrhythmias of selected medical concern and wirelessly sending an alert via the transceiver upon the occurrence of one of the arrhythmias of selected medical concern;

executing heuristics to actively identify or narrow down a pattern or underlying cause of sporadic cardiac conditions and wirelessly sending an alert via the transceiver upon the occurrence of one of the pattern and the underlying cause;

executing programming tailored to the monitoring and medical diagnostic needs of at least one of a specific patient, patient group or general patient population of conditions or symptoms of medical concern and wirelessly sending an alert via the transceiver upon the occurrence of one of the conditions or symptoms of medical concern.

17. A subcutaneous insertable cardiac monitor in accordance with claim 1, further comprising:

a patient-interfaceable component selected from the group comprising an external tactile feedback device that wirelessly interfaces to the insertable cardiac monitor through the transceiver and an external buzzer implemented as part of the external tactile feedback device or as a separate wirelessly-interfaceable component.

18. A subcutaneous insertable cardiac monitor in accordance with claim 1, the pair of ECG sensing electrodes further comprising:

an electrode configuration defining an electrode-to-electrode spacing of between 20 mm to 200 mm.

19. A subcutaneous insertable cardiac monitor in accordance with claim 1, the pair of ECG sensing electrodes further comprising:

an electrode shape comprising a round disc from 2 mm to 10 mm in diameter.

20. A subcutaneous insertable cardiac monitor in accordance with claim 1, wherein the at least one pair of ECG sensing electrodes are provided on a ventral surface and on opposite ends of the implantable housing.

21. A subcutaneous insertable cardiac monitor in accordance with claim 1, wherein the microcontroller is operable to execute under modular micro program control as specified in firmware.

22. A subcutaneous insertable cardiac monitor in accordance with claim 1, wherein the memory is a non-volatile memory.

\* \* \* \* \*